(12) United States Patent
DeLuca et al.

(10) Patent No.: US 7,300,925 B2
(45) Date of Patent: Nov. 27, 2007

(54) 2-ETHYL AND 2-ETHYLIDENE-19-NOR-VITAMIN D COMPOUNDS

(75) Inventors: Hector F. DeLuca, Deerfield, WI (US); Rafal R. Sicinski, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/603,721

(22) Filed: Nov. 22, 2006

(65) Prior Publication Data

US 2007/0088008 A1 Apr. 19, 2007

Related U.S. Application Data

(62) Division of application No. 11/191,791, filed on Jul. 28, 2005, now Pat. No. 7,141,558, which is a division of application No. 10/957,483, filed on Oct. 1, 2004, now Pat. No. 6,992,074, which is a division of application No. 09/871,227, filed on May 31, 2001, now Pat. No. 6,806,262.

(60) Provisional application No. 60/208,199, filed on May 31, 2000.

(51) Int. Cl.
*A61K 31/59* (2006.01)
(52) U.S. Cl. .................... 514/167; 514/863
(58) Field of Classification Search .................. 514/167
See application file for complete search history.

(56) References Cited

U.S. PATENT DOCUMENTS

| | | | |
|---|---|---|---|
| 4,666,634 A | 5/1987 | Miyamoto et al. | 260/397 |
| 5,086,191 A | 2/1992 | DeLuca et al. | 552/653 |
| 5,237,110 A | 8/1993 | DeLuca et al. | 568/665 |
| 5,246,925 A | 9/1993 | DeLuca et al. | 514/167 |
| 5,428,029 A | 6/1995 | Doran et al. | 514/167 |
| 5,484,782 A | 1/1996 | DeLuca et al. | 514/167 |
| 5,536,713 A | 7/1996 | DeLuca et al. | 514/167 |
| 5,587,497 A | 12/1996 | DeLuca et al. | 552/653 |
| 5,817,648 A | 10/1998 | Kutner et al. | 514/167 |
| 5,843,927 A | 12/1998 | DeLuca | 514/167 |
| 5,843,928 A | 12/1998 | DeLuca et al. | 514/167 |
| 5,846,960 A | 12/1998 | Labrie | 514/169 |
| 5,849,726 A | 12/1998 | Brenner | 514/108 |
| 5,877,168 A | 3/1999 | Miyamoto et al. | 514/167 |
| 5,936,133 A | 8/1999 | DeLuca et al. | 568/828 |
| 5,945,410 A | 8/1999 | DeLuca et al. | 514/167 |

FOREIGN PATENT DOCUMENTS

| | | |
|---|---|---|
| EP | 516410 | 12/1982 |
| EP | 184206 | 12/1985 |
| EP | 387077 | 9/1990 |
| EP | 474517 | 11/1992 |
| WO | WO96/01811 | 1/1996 |
| WO | WO98/41500 | 9/1998 |

OTHER PUBLICATIONS

Baggiolini et al, "Stereocontrolled Total Synthesis of 1α,25-Dihydroxycholecalciferol and 1α,25-Dihydroxyerocalciferol,", J. Org. Chem., 51, pp. 3098-3108, 1986.
Bouillon et al, "Biologic Activity of Dihydroxylated 19-Nor-(Pre)Vitamin $D_3$," Bioactivity of 19-Nor-Pre D, vol. 8, No. 8, pp. 1009-1015, 1993.
Chemical Abstracts, "2β-Substituted Vitamin D Derivatives," vol. 121, No. 21, Nov. 21, 1994.
Chemical Abstracts, "Chemistry of Synthetic High Polymers," vol. 110, No. 10, Mar. 6, 1989.
Kiegiel et al, "Chemical Conversion of Vitamin $D_3$ to its 1,25-Dihydroxy Metabolite," Tetrahedron Letters, vol. 31, No. 43, pp. 6057-6060,1991.
Okano et al, "Regulatory Activities of 2β-(3-Hydroxypropoxy)-1α,25-Dihydroxy-Vitamin $D_3$. A Novel Synthetic Vitamin $D_3$ Derivative, on Calcium Metabolism," Biochemical and Biophysical Research Communications, vol. 163, No. 3, pp. 1444-1449, Sep. 29, 1989.
Perlman et al, "1α,25-Dihydroxy-19-Nor-Vitamin $D_3$. A Novel Vitamin D-Related Compound with Potential Therapeutic Activity," Tetrahedron Letters, vol. 31, No. 13, pp. 1823-1824, Feb. 1990.
Posner et al, "2-Fluoroalkyl A-Ring Analogs of 1,25-Dihydroxyvitamin $D_3$. Stereocontrolled Total Synthesis via Intramolecular and Intermolecular Diels-Alder Cycloadditions. Preliminary Biological Testing," J. Org. Chem., 1995, 60, pp. 4617-4628.
Posner et al, "Stereocontrolled Synthesis of a Trihydroxylated A Ring as an Immediate Precursor to 1α,2α25-Trihydroxyvitamin $D_3$," J. Org. Chem. 56, pp. 4339-4341, Apr. 15, 1991.
Sarandeses et al, "Synthesis of 1α,25-Dihydroxy-19-Norprevitamin $D_3$," Tetrahedron Letters, pp. 5445-5448, Apr. 1992.
Sicinski, Rafal R. et al, "New 1α,25-Dihydroxy-19-norvitamin $D_3$ Compounds of High Biological Activity: Synthesis and Biological Evaluation of 2-Hydroxymethyl, 2-Methyl, and 2-Methylene Analogues," J. Med. Chem., 1998, 41, pp. 4662-4672.

*Primary Examiner*—Barbara P. Badio
(74) *Attorney, Agent, or Firm*—Andrus, Sceales, Starke & Sawall, LLP

(57) ABSTRACT

Biologically active 19-nor vitamin D analogs substituted at C-2 in the A-ring with an ethylidene or an ethyl group. These compounds have preferential activity on mobilizing calcium from bone and either high or normal intestinal calcium transport activity which allows their in vivo administration for the treatment of metabolic bone diseases where bone loss is a major concern. These compounds are also characterized by high cell differentiation activity.

16 Claims, 10 Drawing Sheets

1α,25-dihydroxy-2α-methyl-19-norvitamin $D_3$

1α,25-dihydroxy-2-methylene-19-norvitamin $D_3$

1α,25-dihydroxyvitamin $D_3$ 2.12 kcal/mol
(97%)

1.62 kcal/mol
(94%)

2.58 kcal/mol
(99%)

1.85 kcal/mol
(96%)

2-ETHYL AND 2-ETHYLIDENE-19-NOR-VITAMIN D COMPOUNDS

CROSS-REFERENCE TO RELATED APPLICATIONS

This application is a divisional of U.S. patent application Ser. No. 11/191,791, filed Jul. 28, 2005, now U.S. Pat. No. 7,141,558, which in turn is a divisional of U.S. patent application Ser. No. 10/957,483 filed Oct. 1, 2004, now U.S. Pat. No. 6,992,074, which in turn is a divisional of U.S. patent application Ser. No. 09/871,227, filed May 31, 2001, now U.S. Pat. No. 6,806,262, which in turn is based on and claims priority from Provisional Patent Application Ser. No. 60/208,199 filed May 31, 2000.

BACKGROUND OF THE INVENTION

This invention relates to vitamin D compounds, and more particularly to vitamin D derivatives substituted at the carbon 2 position.

The natural hormone, $1\alpha,25$-dihydroxyvitamin $D_3$ and its analog in ergosterol series, i.e. $1\alpha,25$-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., $1\alpha$, 25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlmnan et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of $1\alpha,25$-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of $1\alpha,25$-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of $1\alpha,25$-dihydroxy-19-norvitamin $D_3$ have also been synthesized, i.e. compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

SUMMARY OF THE INVENTION

The discovery of the hormonally active form of vitamin $D_3$, $1\alpha$, 25-dihydroxyvitamin $D_3$ ($1\alpha,25$-$(OH)_2D_3$, calcitriol, 1; FIG. 1), has greatly stimulated research into its physiology and chemistry. As previously noted, it has been established that 1 not only regulates the mineral metabolism in animals and humans, but also exerts potent effects upon cell proliferation and cellular differentiation. Therefore, the chemistry of vitamin D has been recently focused on the design and synthesis of analogs that can exert selective biological actions.

In a previous investigation of the structure-activity relationship of the vitamin D molecule, an analog of the natural hormone 1, $1\alpha,25$-dihydroxy-2-methylene-19-norvitamin $D_3$ (2), was prepared in which the exocyclic methylene group is transposed, in comparison with 1, from C-10 to C-2. Also, $2\alpha$-methyl analog 3 was obtained by selective hydrogenation of 2. Both analogs were characterized by significant biological potency, enhanced especially in their isomers in the 20S-series.

In a continuing search for biologically active vitamin D compounds novel 19-nor analogs of 1, substituted at C-2 with ethylidene (4a,b and 5a,b) and ethyl (6a,b and 7a,b) groups, have now been synthesized and tested. Structurally the novel 2-ethylidene analogs belong to a class of 19-nor vitamin D compounds characterized by the general formula I shown below:

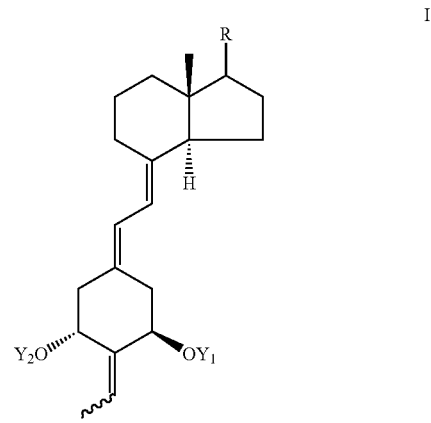

where $Y_1$ and $Y_2$, which may be the same or different, are each selected from the group consisting of hydrogen and a hydroxy-protecting group, and where the group R represents any of the typical side chains known for vitamin D type compounds.

Structurally the novel 2-ethyl analogs belong to a class of 19-nor vitamin D compounds characterized by the general formula II shown below:

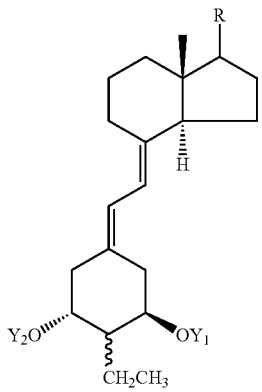

II where $Y_1$ and $Y_2$, which may be the same or different, are each selected from the group consisting of hydrogen and a hydroxy-protecting group, and where the group R represents any of the typical side chains known for vitamin D type compounds.

More specifically R can represent a saturated or unsaturated hydrocarbon radical of 1 to 35 carbons, that may be straight-chain, branched or cyclic and that may contain one or more additional substituents, such as hydroxy-or protected-hydroxy groups, fluoro, carbonyl, ester, epoxy, amino or other heteroatomic groups. Preferred side chains of this type are represented by the structure below:

where the stereochemical center (corresponding to C-20 in steroid numbering) may have the R or S configuration, (i.e. either the natural configuration about carbon 20 or the 20-epi configuration), and where Z is selected from Y, —OY, —$CH_2OY$, —C≡CY, —QH=CHY, and —$CH_2CH_2CH$=$CR^3R^4$, where the double bond may have the cis or trans geometry, and where Y is selected from hydrogen, methyl, —$COR^5$ and a radical of the structure:

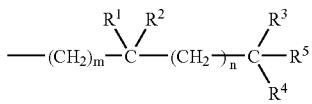

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, $C_{1-5}$ alkyl or —$OR^7$ where $R^7$ represents $C_{1-5}$ alkyl, and wherein any of the CH-groups at positions 20, 22, or 23 in the side chain may be replaced by a nitrogen atom, or where any of the groups —$CH(CH_3)$—, —$CH(R^3)$—, or —CH($R^2$)— at positions 20, 22, and 23, respectively, may be replaced by an oxygen or sulfur atom.

The wavy lines, e.g. to the substituents at C-2 and at C-20 indicate that those substituents may have either the R or S configuration.

Specific important examples of side chains with natural 20R-configuration are the structures represented by formulas (a), b), (c), (d) and (e) below. i.e. the side chain as it occurs in 25-hydroxyvitamin $D_3$ (a); vitamin $D_3$ (b); 25-hydroxyvitamin $D_2$ (c); vitamin $D_2$ (d); and the C-24 epimer of 25-hydroxyvitamin $D_2$ (e):

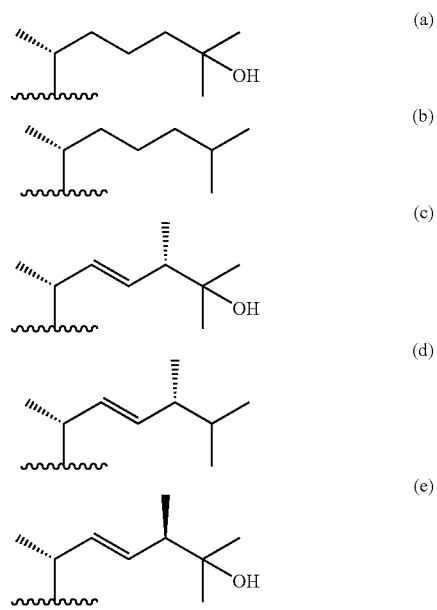

Specific important examples of side chains with the unnatural 20S (also referred to as the 20-epi) configuration are the structures presented by formulas (f), (g), (h), (i) and (j) below:

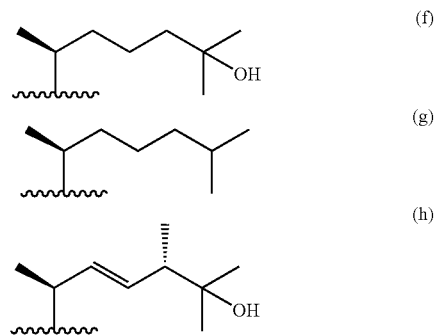

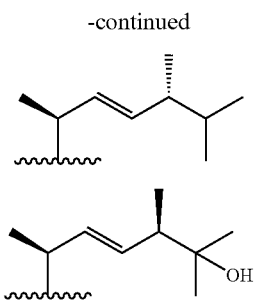

The above novel compounds exhibit a desired, and highly advantageous, pattern of biological activity. The synthesized vitamins were tested for their ability to bind the porcine intestinal vitamin D receptor. The presented results (FIG. 5) indicate that 2-ethylidene-19-norvitamins, possessing methyl group from ethylidene moiety directed toward C-3, i.e., trans in relation to C(6)-C(7) bond (isomers E), are more active than $1\alpha,25\text{-}(OH)_2D_3$ in binding to VDR, whereas their counterparts with cis relationship between ethylidene methyl substituent and C(7)-H group (isomers Z) exhibit significantly reduced affinity for the receptor. The competitive binding analysis showed also that $2\alpha$-ethyl-19-norvitamins bind to the receptor better than their isomers with $2\beta$-ethyl substituents (FIG. 6). In the next assay, the cellular activity of the synthesized compounds was established by studying their ability to induce differentiation of human promyelocyte HL-60 cells into monocytes. E isomer of (20S)-2-ethylidene-19-norvitamin $D_3$ (FIG. 7) and both $2\alpha$-ethyl-19-norvitamins (FIG. 8) are more potent than $1\alpha,25\text{-}(OH)_2D_3$ in this assay, whereas the remaining tested compounds are almost equivalent to the hormone 1. Both E isomers of 2-ethylidene-19-norvitamins, when tested in vivo in rats (Table 1) exhibited very high calcemic activity, the (20S)-compound being especially potent. On the contrary, isomeric Z compounds are significantly less active. 2-Ethyl-19-norvitamins have some ability to mobilize calcium from bone but not to the extent of the hormone 1, while being inactive in intestine. The only exception is the $2\alpha$-ethyl isomer from the 20S-series which shows strong calcium mobilization response and marked intestinal activity.

These compounds are thus highly specific in their calcemic activity. Their preferential activity on mobilizing calcium from bone and either high or normal intestinal calcium transport activity allows the in vivo administration of these compounds for the treatment of metabolic bone diseases where bone loss is a major concern. Because of their preferential calcemic activity on bone, these compounds would be preferred therapeutic agents for the treatment of diseases where bone formation is desired, such as osteoporosis, especially low bone turnover osteoporosis, steroid induced osteoporosis, senile osteoporosis or postmenopausal osteoporosis, as well as osteomalacia and renal osteodystrophy. The treatment may be transdermal, oral or parenteral. The compounds may be present in a composition in an amount from about 0.1 μg/gm to about 50 μkg/gm of the composition, and may be administered in dosages of from about 0.01 μg/day to about 50 μg/day.

The compounds of the invention are also especially suited for treatment and prophylaxis of human disorders which are characterized by an imbalance in the immune system, e.g. in autoimmune diseases, including multiple sclerosis, diabetes mellitus, host versus graft reaction, lupus, atherosclerosis, and rejection of transplants; and additionally for the treatment of inflammatory diseases, such as inflammatory bowel disease, rheumatoid arthritis and asthma, as well as the improvement of bone fracture healing and improved bone grafts. Acne, alopecia especially chemically induced alopecia (e.g. resulting from chemotherapy), skin conditions such as dermatitis, eczema, keratosis, dry skin (lack of dermal hydration), undue skin slackness (insufficient skin firmness), insufficient sebum secretion and wrinkles, as well as hypocalcemia, hypoparathyroidism and hypertension are other conditions which may be treated with the compounds of the invention.

The above compounds are also characterized by high cell differentiation activity. Thus, these compounds also provide therapeutic agents for the treatment of psoriasis, or as an anti-cancer agent, especially against leukemia, colon cancer,.breast cancer and prostate cancer. The compounds may be present in a composition to treat psoriasis, cancer, and/or the above list of diseases in an amount from about 0.01 μg/gm to about 100 μg/gm of the composition, and may be administered topically, transdermally, orally or parenterally in dosages of from about 0.01 μg/day to about 100 μg/day.

This invention also provides novel intermediate compounds formed during the synthesis of the end products.

This invention also provides a novel synthesis for the production of the end products of structures I and II. Two different synthetic paths were devised, both based on Lythgoe type Wittig-Horner coupling of the A-ring fragments, the corresponding phosphine oxides prepared from quinic acid, with the protected 25-hydroxy Grundmann's ketone. In the first method, the allylic phosphine oxides were substituted at C-4' with the ethylidene group whereas in the alternative approach the introduction of ethylidene moiety was performed in the final step of the synthesis, by Wittig reaction of the intermediate 2-oxo-vitamin D analog. The selective catalytic hydrogenation of 2-ethylidene analogs of $1\alpha,25$-dihydroxy-19-norvitamin $D_3$ provided the corresponding $2\alpha$-and $2\beta$-ethyl compounds.

A-ring conformations of the synthesized analogs: 4a,b (b), 5a,b (c), 6a,b (d) and 7a,b (e).

Figure 5A:
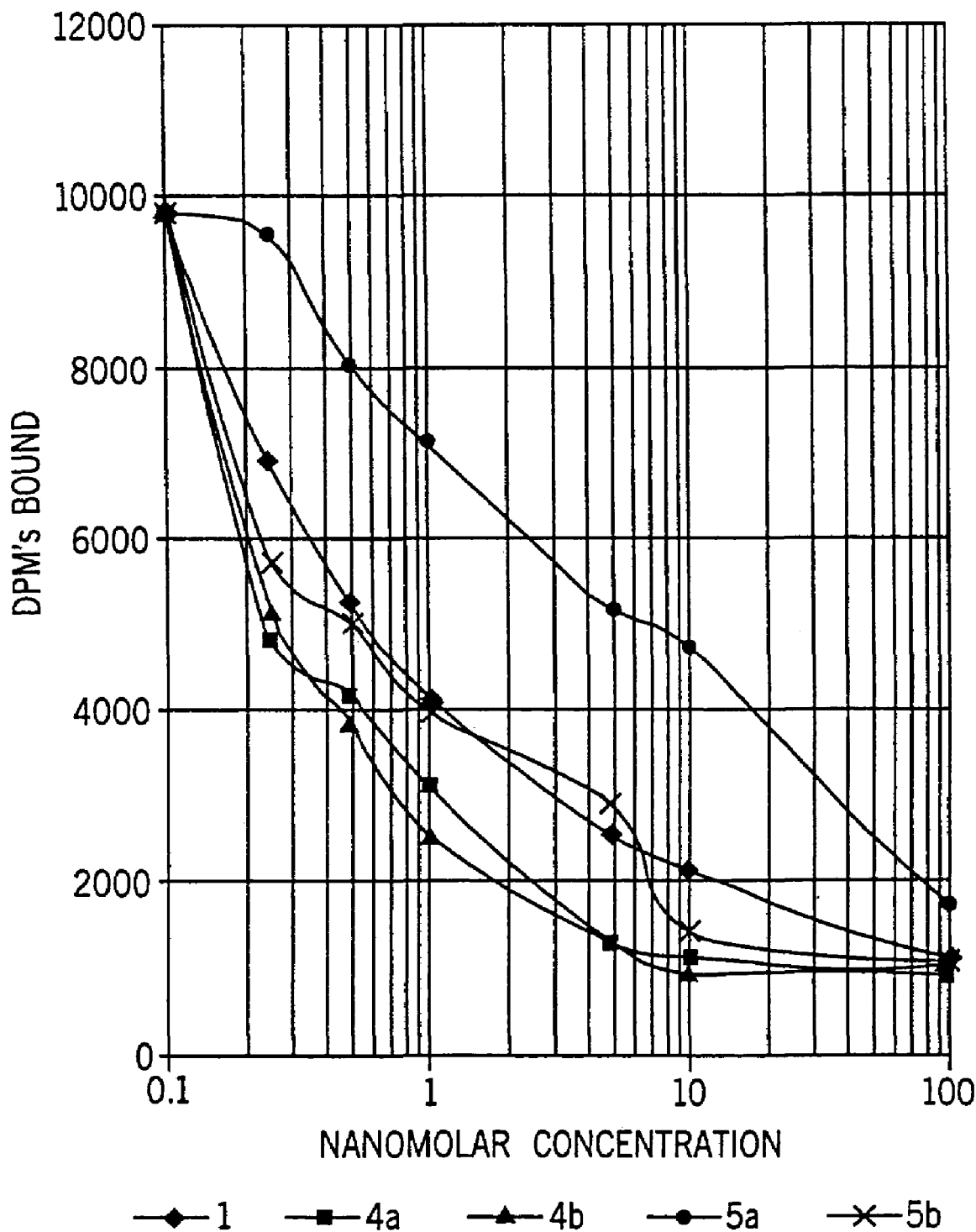
Figure 5B:
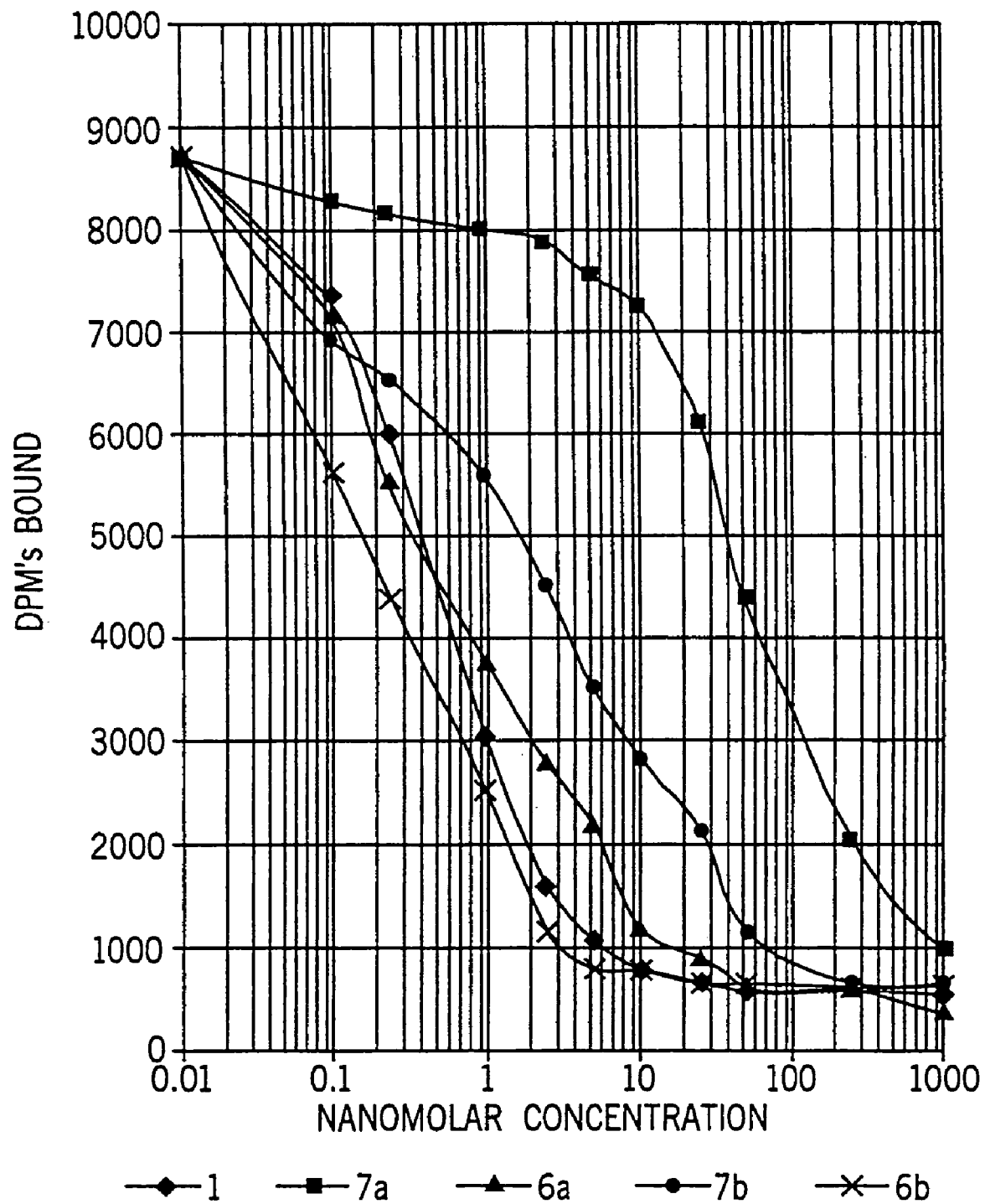
Figure 6A:
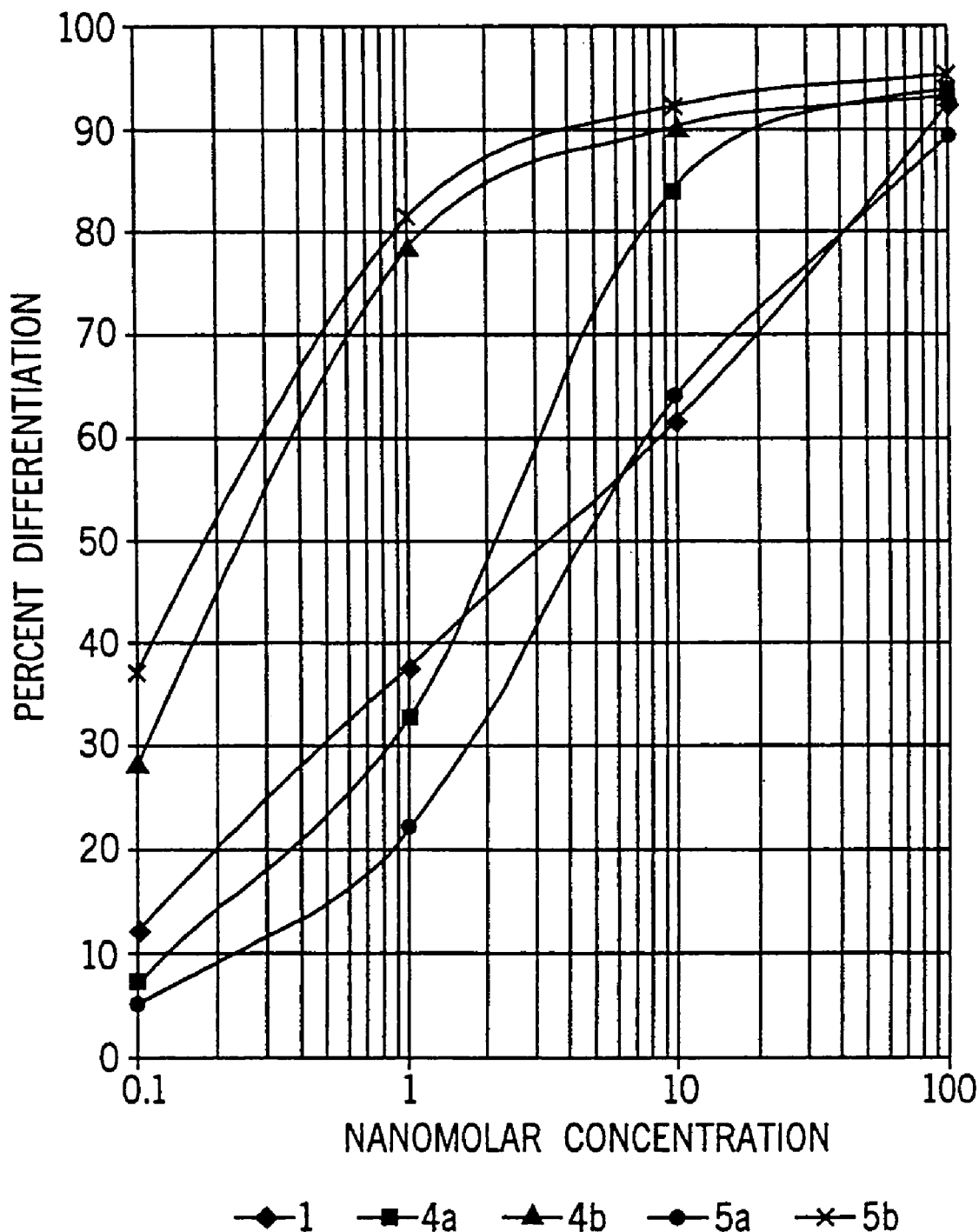
Figure 6B:
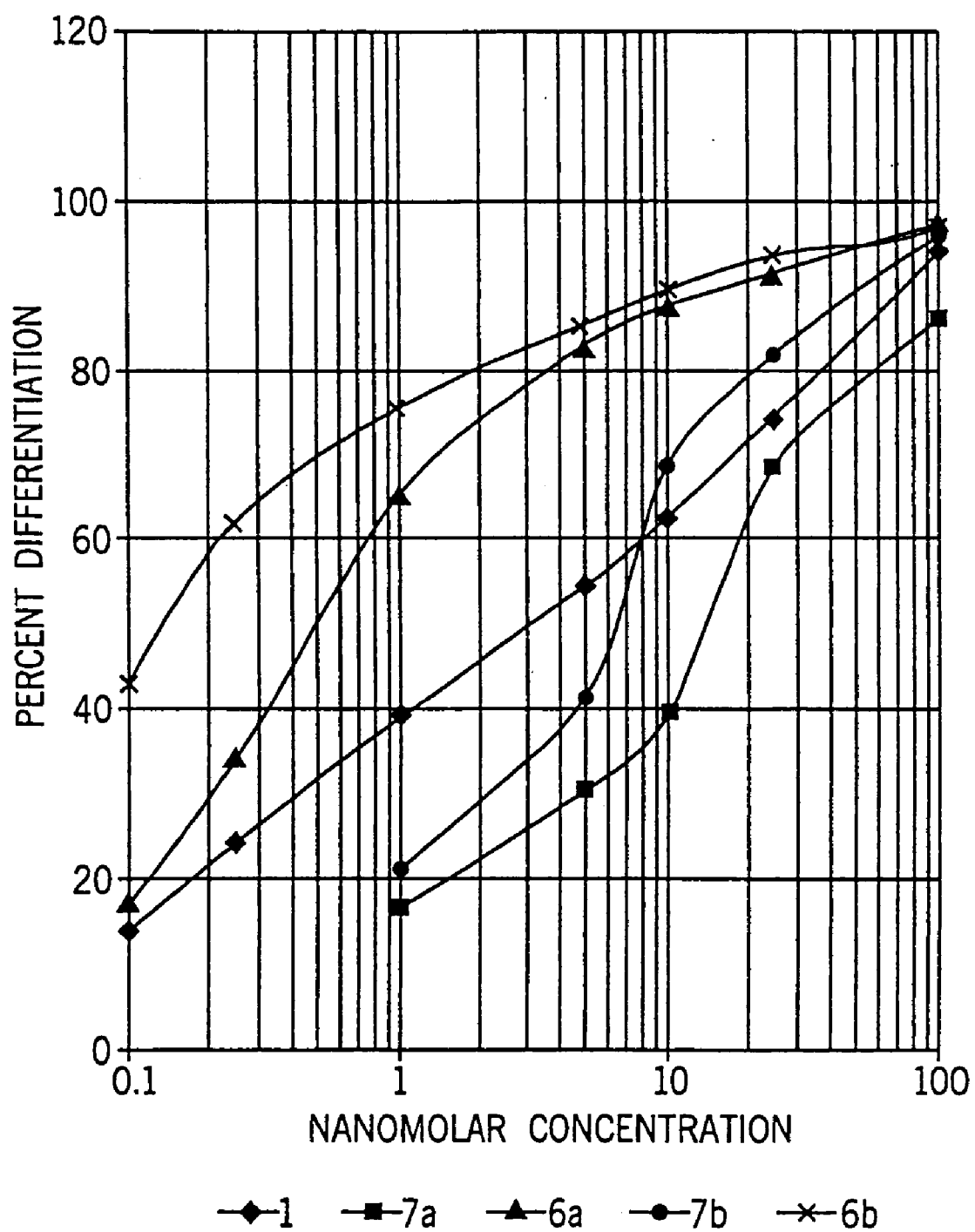

FIG. 5a is a graph illustrating the relative activity of a 2-ethylidene-19-nor-vitamins (isomers E and Z) and 1α,25-dihydroxyvitamin $D_3$ to compete for binding of [$^3$H]-1,25-$(OH)_2$-$D_3$ to the pig intestinal nuclear vitamin D receptor;

FIG. 5b is a graph similar to FIG. 5a except illustrating the relative activity of individual compounds 2α and 2β-ethyl-19-nor-vitamins and 1α,25-dihydroxyvitamin $D_3$ to compete for binding of [$^3$H]-1,25-$(OH)_2$-$D_3$ to the vitamin D pig intestinal nuclear receptor;

FIG. 6a is a graph illustrating the percent HL-60 cell differentiation as a function of the concentration of the 2-ethylidene-19-nor-vitamins as compared to 1α,25-dihydroxyvitamin D3; and FIG. 6b is a graph illustrating the percent HL-60 cell differentiation as a function of the concentration of the 2α and 2β-ethyl-19-nor-vitamins as compared to 1α,25-dihydroxyvitamin $D_3$.

DETAILED DESCRIPTION OF THE INVENTION

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro-or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R^3$ and $R^4$ are ethyl groups. Likewise, the term "26,27-diethyl" refers to the addition of an ethyl group at the 26 and 27 positions so that $R^3$ and $R^4$ are propyl groups.

In the following lists of compounds, the particular isometric form of the ethylidene substituent attached at the carbon 2 position should be added to the nomenclature. For example, if the methyl group of the ethylidene substituent is in its (E) configuration, then the term "2(E)" should be included in each of the named compounds. If the methyl group of the ethylidene substituent is in its (Z) configuration, then the term "2(Z)" should be included in each of the named compounds. In addition, if the methyl group attached at the carbon 20 position is in its epi or unnatural configuration, the term "20(S)" or "20-epi" should be included in each of the following named compounds. Also, if the side chain contains an oxygen atom substituted at any of positions 20, 22 or 23, the term "20-oxa", "22-oxa" or "23-oxa", respectively, should be added to the named compound. The named compounds could also be of the vitamin $D_2$ or $D_4$ type if desired.

Specific and preferred examples of the 2-ethylidene-compounds of structure I when the side chain is unsaturated are:

2-ethylidene-19-nor-1,25-dihydroxy-22,23-dehydrovitamin $D_3$;

2-ethylidene-19-nor-24-homo-1,25-dihydroxy-22,23-dehydrovitamin $D_3$;

2-ethylidene-19-nor-24-dihomo-1,25-dihydroxy-22,23-dehydrovitamin $D_3$;

2-ethylidene-19-nor-24-trihomo-1,25-dihydroxy-22,23-dehydrovitamin $D_3$;

2-ethylidene-19-nor-26,27-dimethyl-24-homo-1,25-dihydroxy-22,23-dehydrovitamin $D_3$;

2-ethylidene-19-nor-26,27-dimethyl-24-dihomo-1,25-dihydroxy-22,23-dehydrovitamin $D_3$;

2-ethylidene-19-nor-26,27-dimethyl-24-trihomo-1,25-dihydroxy-22,23-dehydrovitamin $D_3$;

2-ethylidene-19-nor-26,27-diethyl-24-homo-1,25-dihydroxy-22,23-dehydrovitamin $D_3$;

2-ethylidene-19-nor-26,27-diethyl-24-dihomo-1,25-dihydroxy-22,23-dehydrovitamin $D_3$;

2-ethylidene-19-nor-26,27-diethyl-24-trihomo-1,25-dihydroxy-22,23-dehydrovitamin $D_3$;

2-ethylidene-19-nor-26,27-dipropoyl-24-homo-1,25-dihydroxy-22,23-dehydrovitamin $D_3$;

2-ethylidene-19-nor-26,27-dipropyl-24-dihomo-1,25-dihydroxy-22,23-dehydrovitamin $D_3$; and 2-ethylidene-19-nor-26,27-dipropyl-24-trihomo-1,25-dihydroxy-22,23-dehydrovitamin $D_3$.

With respect to the above unsaturated compounds, it should be noted that the double bond located between the 22 and 23 carbon atoms in the side chain may be in either the (E) or (Z) configuration. Accordingly, depending upon the configuration, the term "22,23(E)" or "22,23(Z)" should be included in each of the above named compounds. Also, it is common to designate the double bond located between the 22 and 23 carbon atoms with the designation "$\Delta^{22}$". Thus, for example, the first named compound above could also be written as 2-ethylidene-19-nor-22,23(E)-$\Delta^{22}$-1,25-$(OH)_2D_3$ where the double bond is in the (E) configuration. Similarly, if the methyl group attached at carbon 20 is in the unnatural configuration, this compound could be written as 2-ethylidene-19-nor-20(S)-22,23(E)-$\Delta^{22}$-1,25-$(OH)_2D_3$.

Specific and preferred examples of the 2-ethylidene-compounds of structure I when the side chain is saturated are:

2-ethylidene-19-nor-1,25-dihydroxyvitamin $D_3$;

2-ethylidene-19-nor-24-homo-1,25-dihydroxyvitamin $D_3$;

2-ethylidene-19-nor-24-dihomo-1,25-dihydroxyvitamin $D_3$;

2-ethylidene-19-nor-24-trihomo-1,25-dihydroxyvitamin $D_3$;

2-ethylidene-19-nor-26,27-dimethyl-24-homo-1,25-dihydroxyvitamin $D_3$;

2-ethylidene-19-nor-26,27-dimethyl-24-dihomo-1,25-dihydroxyvitamin $D_3$;

2-ethylidene-19-nor-26,27-dimethyl-24-trihomo-1,25-dihydroxyvitamin $D_3$;

2-ethylidene-19-nor-26,27-diethyl-24-homo-1,25-dihydroxyvitamin $D_3$;

2-ethylidene-19-nor-26,27-diethyl-24-dihomo-1,25-dihydroxyvitamin $D_3$;

2-ethylidene-19-nor-26,27-diethyl-24-trihomo-1,25-dihydroxyvitamin $D_3$;

2-ethylidene-19-nor-26,27-dipropyl-24-homo-1,25-dihydroxyvitamin $D_3$;

2-ethylidene-19-nor-26,27-dipropyl-24-dihomo-1,25-dihydroxyvitamin $D_3$; and 2-ethylidene-19-nor-26,27-dipropyl-24-trihomo-1,25-dihydroxyvitamin $D_3$.

As noted previously, the above saturated side chain compounds should have the appropriate 2(E) or 2(Z) configuration and/or carbon 20 configuration added to the nomenclature. For example, particularly preferred compounds are:

19-nor-2(E)-ethylidene-1α,25-dihydroxyvitamin $D_3$;
19-nor-2(Z)-ethylidene-1α,25-dihydroxyvitamin $D_3$;
19-nor-2(E)-ethylidene-20(S)-1α,25-dihydroxyvitamin $D_3$; and
19-nor-2(Z)-ethylidene-20(S)-1α,25-dihydroxyvitamin $D_3$.

In the following lists of compounds, the particular isometric form of the ethyl substituent attached at the carbon 2 position should be added to the nomenclature. For example, if the ethyl group is in the alpha configuration, the term "2α-methyl" should be included in each of the named compounds. If the ethyl group is in the beta configuration, the term "2β-ethyl" should be included in each of the named compounds. In addition, if the methyl group attached at the carbon 20 position is in its epi or unnatural configuration, the term "20(S)" or "20-epi" should be included in each of the following named compounds. Also, if the side chain contains an oxygen atom substituted at any of positions 20, 22 or 23, the term "20-oxa," "22-oxa" or "23-oxa," respectively, should be added to the named compound. The named compounds could also be of the vitamin $D_2$ or $D_4$ type if desired.

Specific and preferred examples of the 2-ethyl-compounds of structure II when the side chain is unsaturated are:

2-ethyl-19-nor-1,25-dihydroxy-22,23-dehydrovitamin $D_3$;

2-ethyl-19-nor-24-homo-1,25-dihydroxy-22,23-dehydrovitamin $D_3$;

2-ethyl-19-nor-24-dihomo-1,25-dihydroxy-22,23-dehydrovitamin $D_3$;

2-ethyl-19-nor-24-trihomo-1,25-dihydroxy-22,23-dehydrovitamin $D_3$;

2-ethyl-19-nor-26,27-dimethyl-24-homo-1,25-dihydroxy-22,23-dehydrovitamin $D_3$;

2-ethyl-19-nor-26,27-dimethyl-24-dihomo-1,25-dihydroxy-22,23-dehydrovitamin $D_3$;

2-ethyl-19-nor-26,27-dimethyl-24-trihomo-1,25-dihydroxy-22,23-dehydrovitamin $D_3$;

2-ethyl-19-nor-26,27-diethyl-24-homo-1,25-dihydroxy-22,23-dehydrovitamin $D_3$;

2-ethyl-19-nor-26,27-diethyl-24-dihomo-1,25-dihydroxy-22,23-dehydrovitamin $D_3$;

2-ethyl-19-nor-26,27-diethyl-24-trihomo-1,25-dihydroxy-22,23-dehydrovitamin $D_3$;

2-ethyl-19-nor-26,27-dipropoyl-24-homo-1,25-dihydroxy-22,23-dehydrovitamin $D_3$;

2-ethyl-19-nor-26,27-dipropyl-24-dihomo-1,25-dihydroxy-22,23-dehydrovitamin $D_3$; and 2-ethyl-19-nor-26,27-dipropyl-24-trihomo-1,25-dihydroxy-22,23-dehydrovitamin $D_3$.

With respect to the above unsaturated compounds, it should be noted that the double bond located between the 22 and 23 carbon atoms in the side chain may be in either the (E) or (Z) configuration. Accordingly, depending upon the configuration, the term "22,23(E)" or "22,23(Z)" should be included in each of the above named compounds. Also, it is common to designate the double bond located between the 22 and 23 carbon atoms with the designation "$\Delta^{22}$". Thus, for example, the first named compound above could also be written as 2-ethyl-19-nor-22,23(E)-$\Delta^{22}$-1,25-(OH)$_2$D$_3$ where the double bond is in the (E) configuration. Similarly, if the methyl group attached at carbon 20 is in the unnatural configuration, this compound could be written as 2-ethyl-19-nor-20(S)-22,23(E)-$\Delta^{22}$-1,25-(OH)$_2$D$_3$.

Specific and preferred examples of the 2-ethyl-compounds of structure II when the side chain is saturated are:

2-ethyl-19-nor-1,25-dihydroxyvitamin $D_3$;
2-ethyl-19-nor-24-homo-1,25-dihydroxyvitamin $D_3$;
2-ethyl-19-nor-24-dihomo-1,25-dihydroxyvitamin $D_3$;
2-ethyl-19-nor-24-trihomo-1,25-dihydroxyvitamin $D_3$;
2-ethyl-19-nor-26,27-dimethyl-24-homo-1,25-dihydroxyvitamin $D_3$;
2-ethyl-19-nor-26,27-dimethyl-24-dihomo-1,25-dihydroxyvitamin $D_3$;
2-ethyl-19-nor-26,27-dimethyl-24-trihomo-1,25-dihydroxyvitamin $D_3$;
2-ethyl-19-nor-26,27-diethyl-24-homo-1,25-dihydroxyvitamin $D_3$;
2-ethyl-19-nor-26,27-diethyl-24-dihomo-1,25-dihydroxyvitamin $D_3$;
2-ethyl-19-nor-26,27-diethyl-24-trihomo-1,25-dihydroxyvitamin $D_3$;
2-ethyl-19-nor-26,27-dipropyl-24-homo-1,25-dihydroxyvitamin $D_3$;
2-ethyl-19-nor-26,27-dipropyl-24-dihomo-1,25-dihydroxyvitamin $D_3$; and
2-ethyl-19-nor-26,27-dipropyl-24-trihomo-1,25-dihydroxyvitamin $D_3$.

As noted previously, the above saturated side chain compounds should have the appropriate 2α-or 2β-configuration and/or carbon 20 configuration added to the nomenclature. For example, particularly preferred compounds are:

19-nor-2α-ethyl-1α,25-dihydroxyvitamin $D_3$;
19-nor-2β-ethyl-1α,25-dihydroxyvitamin $D_3$;
19-nor-20(S)-2α-ethyl-1α,25-dihydroxyvitamin $D_3$; and
19-nor-20(S)-2β-ethyl-1α,25-dihydroxyvitamin $D_3$.

The preparation of 2-ethylidene-19-nor-vitamin D compounds, and the 2-ethyl-19-nor-vitamin D compounds, having the basic structure I and II can be accomplished by a common general method, i.e. the condensation of a bicyclic Windaus-Grundmann type ketone III with the allylic phosphine oxide IVa or IVb to the corresponding 2-ethylidene-19-nor-vitamin D analogs Va or Vb, respectively followed by a selective reduction of the ethylidene group at C-2 to the corresponding 2-ethyl compounds.

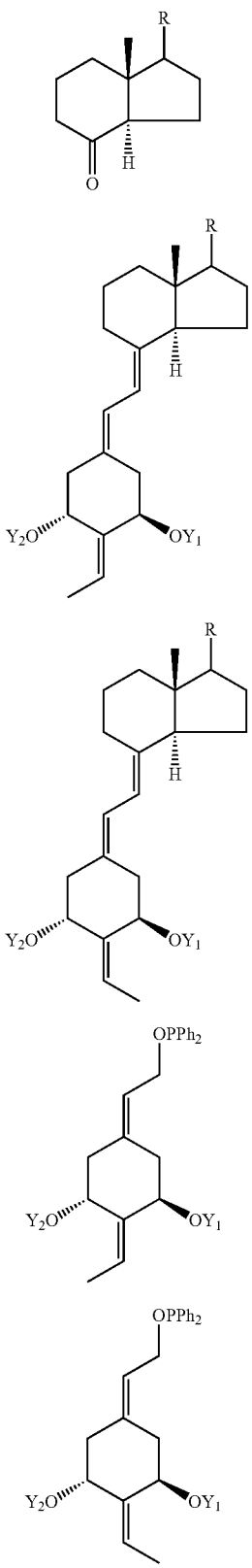

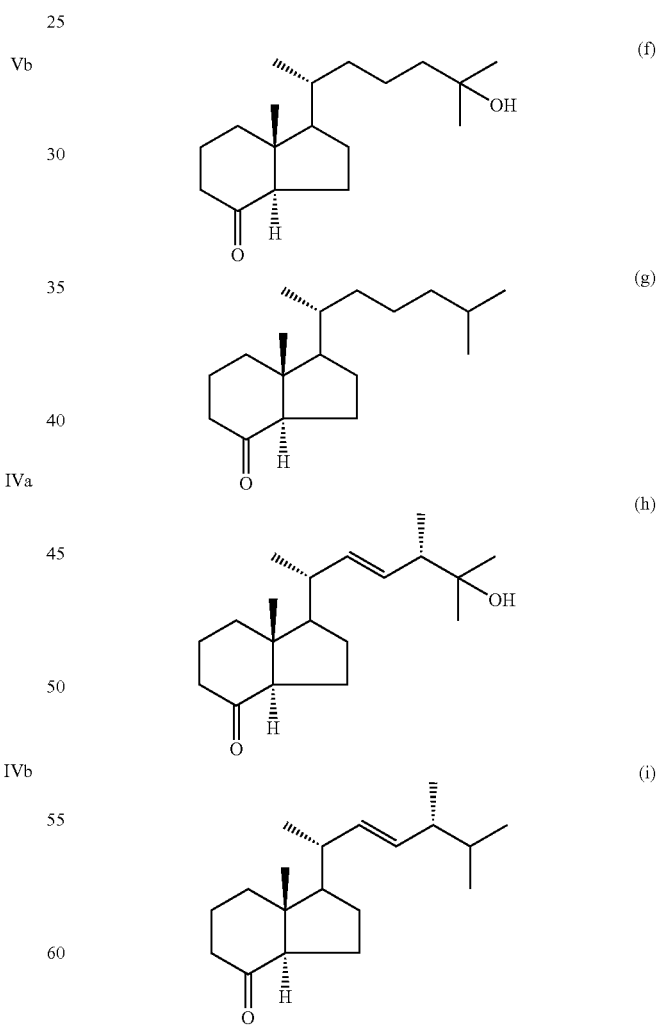

hydroxy-protecting groups, it being also understood that any functionalities in R that might be sensitive, or that interfere with the condensation reaction, be suitable protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51 , 1269 (1986); DeLuca et al., U.S. Pat. No. 5,086,191; DeLuca et al., U.S. Pat. No. 5,536,713].

Hydrindanones of the general structure m are known, or can be prepared by known methods. Specific important examples of such known bicyclic ketones are the structures with the side chains (a), (b), (c) and (d) described above, i.e. 25-hydroxy Grundmann's ketone (f) [Baggiolini et al., J. Org. Chem, 51, 3098 (1986)]; Grundmann's ketone (g) [Inhoffen et al., Chem. Ber. 90, 664 (1957)]; 25-hydroxy Windaus ketone (h) [Baggiolini et al., J. Org. Chem., 51, 3098 (1986)] and Windaus ketone (i) [Windaus et al., Ann., 524, 297 (1936)]:

In the structures III, IV, and V groups $Y_1$ and $Y_2$ and R represent groups defined above; $Y_1$ and $Y_2$ are preferably For the preparation of the required phosphine oxides of general structure IV, a new synthetic route has been developed starting from methyl quinicate derivative 9, easily obtained from commercial (1R,3R,4S,5R)-(−)-quinic acid 8 as described by Perlman et al., Tetrahedron Lett. 32, 7663 (1991) and DeLuca et al., U.S. Pat. No. 5,086,191. The overall process of transformation of the starting methyl ester 9 into the desired A-ring synthons, is summarized by the Scheme I. Reduction of the ester 9 with diisobutylaluminum hydride (DIBALH) or other suitable reducing agent (e.g. lithium aluminum hydride) provided the diol 10 which was subsequently oxidized by sodium periodate to the cyclohexanone ketone derivative 11. Then, the secondary 4-hydroxyl group of 11 was oxidized with $RuO_4$ (a catalytic method with $RuCl_3$ and $NaIO_4$ as co-oxidant). Use of such a strong oxidant was necessary for an effective oxidation process of this very hindered hydroxyl. However, other more commonly used oxidants can also be applied (e.g. pyridinium dichromate), although the reactions usually require much longer time for completion. The next step of the process comprises the Peterson reaction of the ketone 12 with methyl(trimethylsilyl)acetate to form ester 13.

Referring now to Scheme 2, the next step of the synthesis comprises the Wittig reaction of the sterically hindered 4-keto compound 13 with ylide prepared from ethyltriphenylphosphonium bromide and n-butyllithium leading to ethylidene compounds 14 and 15. Ethylidene compounds 14 and 15 in turn were treated with diisobutylaluminum hydride and the formed alcohols 16 and 17 were in turn transformed to the desired A-ring phosphine oxides 18 and 19. Conversion of 16 and 17, to 18 and 19, respectively involved 3 steps, namely, in situ tosylation with n-butyllithium and p-toluenesulfonyl chloride, followed by reaction with diphenylphosphine lithium salt and oxidation with hydrogen peroxide.

Several 2-ethylidene-19-nor-vitamin D compounds of the general structure V may be synthesized using the A-ring synthons 18 and 19 and the appropriate Windaus-Grundmann ketone III having the desired side chain structure. Thus, for example, Scheme 3 illustrates that Wittig-Horner coupling of the phosphinoxy 18 with the protected 25-hydroxy Grundmann's ketone 20 prepared according to published procedure [Sicinski et al., J. Med. Chem. 37, 3730 (1994)] gave the expected protected vitamin compound 21. This, after deprotection afforded 1α,25-dihydroxy-2(E)-ethylidene-19-nor-vitamin $D_3$ (4a). Similarly, Scheme 3 illustrates the synthesis of 1α,25-dihydroxy-2(Z)-ethylidene-19-nor-vitamin $D_3$(5a) from phosphinoxy 19 and Grundmann's ketone 20.

Referring now to Scheme 6, the final step of the process was the selective homogeneous catalytic hydrogenation of the ethylidene unit at carbon 2 in the vitamins 4a and 5a performed efficiently in the presence of tris(triphenylphosphine)rhodium(I) chloride [Wilkinson's catalyst, $(Ph_3P)_3RhCl$]. Such reduction conditions allowed to reduce only $C(2)=CH_2$ unit leaving C(5)—C(8) butadiene moiety unaffected. The isolated material is an epimeric mixture (ca. 1:1) of 2-ethyl-19-nor-vitamins 6a and 7a differing in configuration at C-2. The mixture can be used without separation or, if desired, the individual 2α-and 2β-isomers can be separated by an efficient HPLC system.

The C-20 epimerization may be accomplished by the analogous coupling of the phosphine oxides 18 and 19 with protected 20(S)-25-hydroxy Grundmann's ketone 26 (Scheme 5) which after hydrolysis of the hydroxy-protecting groups gave 20(S)-1α,25-dihydroxy-2-ethylidene-19-nor-vitamin $D_3$ compounds 4b and 5b. Hydrogenation of 4b and 5b provided the expected mixture of the 2-ethyl-19-nor-vitamin D analogs 6b and 7b.

As noted above, other 2-ethylidene and 2-ethyl-19-nor-vitamin D analogs may be synthesized by the method disclosed herein. For example, 1α-hydroxy-2-ethylidene-19-nor-vitamin $D_3$ can be obtained by providing the Grundmann's ketone (g). Subsequent reduction of the A-ring ethylidene group in the formed compound can also give the corresponding epimeric mixture of 1α-hydroxy-2-ethyl-19-nor-vitamin $D_3$ compounds.

A number of oxa-analogs of vitamin $D_3$ and their synthesis are also known. For example, 20-oxa analogs are described in N. Kubodera at al, Chem. Pharm. Bull., 34, 2286 (1986), and Abe et al, FEBS Lett. 222,58, 1987. Several 22-oxa analogs are described in E. Murayama et al, Chem. Pharm. Bull., 34, 4410 (1986), Abe et al, FEBS Lett., 226, 58 (1987), PCT International Application No. WO 90/09991 and European Patent Application, publication number 184 112, and a 23-oxa analog is described in European Patent Application, publication number 78704, as well as U.S. Pat. No. 4,772,433.

This invention is described by the following illustrative examples. In these examples specific products identified by Arabic numerals (e.g. 1, 2, 3, etc) refer to the specific structures so identified in the preceding description and in the Schemes.

EXAMPLE 1

Chemistry

Figure 1C:
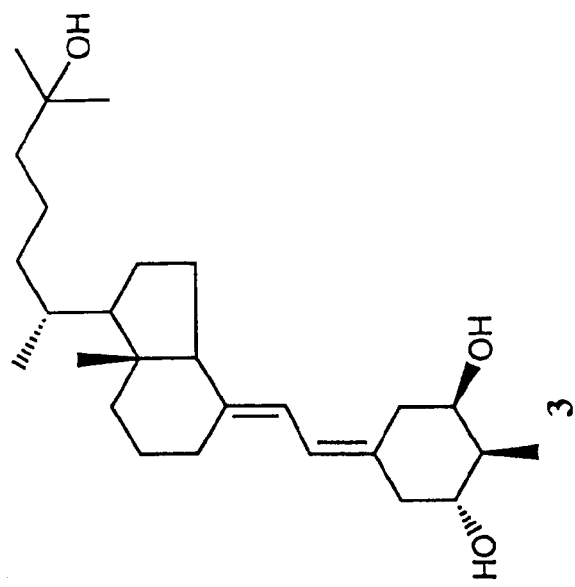
FIG. 1 illustrates the general structural formulae for $1\alpha,25$-dihydroxyvitamin $D_3$, $1\alpha,25$-dihydroxy-2-methylene-19-norvitamin $D_3$, and $1\alpha,25$-dihydroxy-$2\alpha$-methyl-19-norvitamin $D_3$, and further illustrates the general structural formulae for the four 2-ethylidene-19-nor-vitamins and the four 2-ethyl-19-nor-vitamins of the present invention synthesized and tested herein.
Figure 1B:
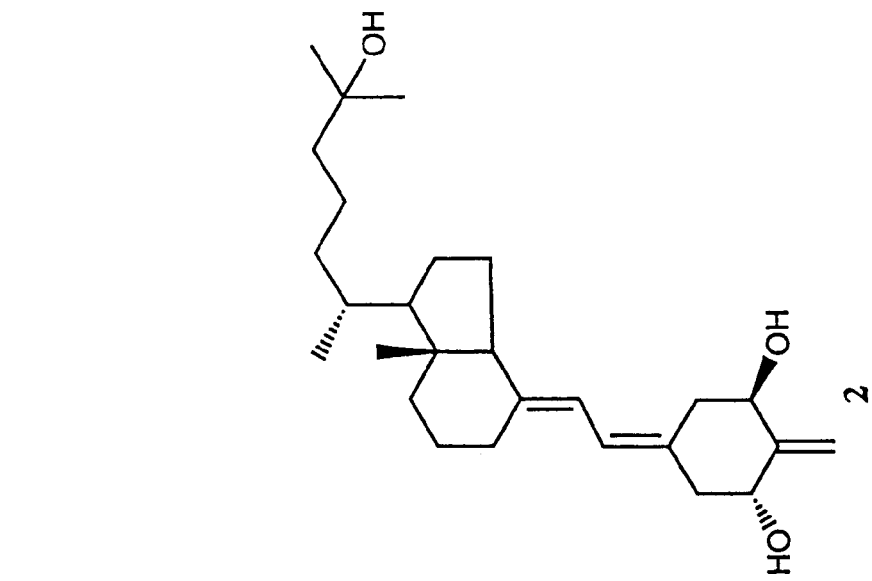
Figure 1A:
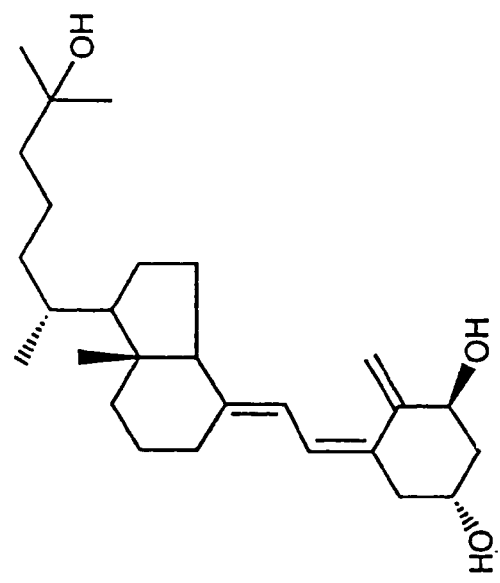
Figure 1D:
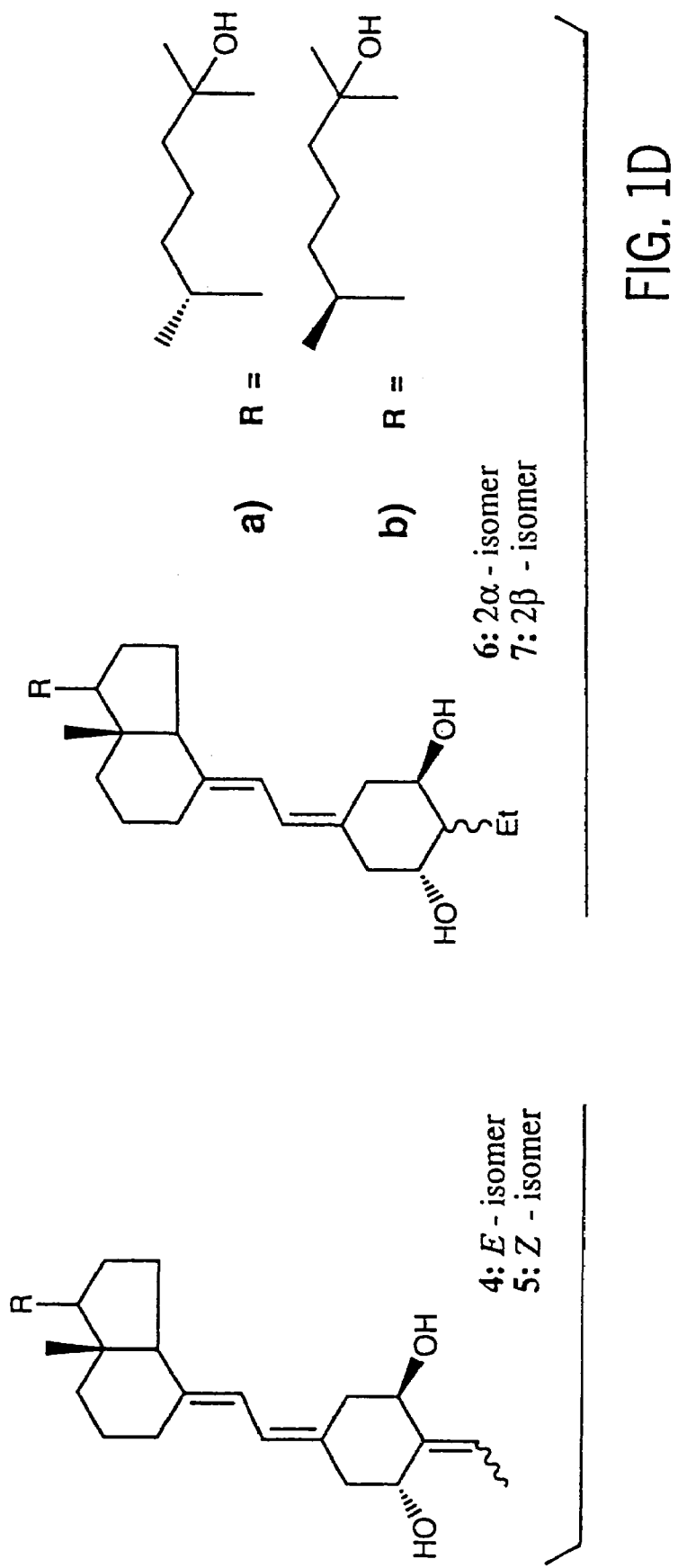
Figure 2A:
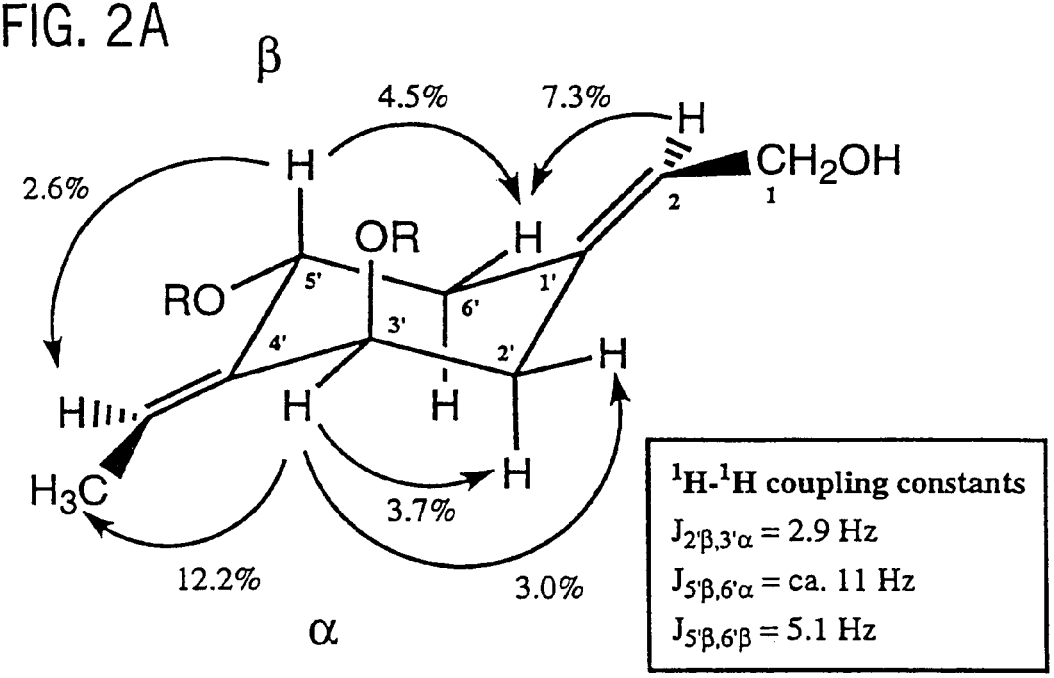
FIG. 2 illustrates the -configurations and preferred conformations of the 4'-ethylidene intermediates 16 and 17 used in the synthesis disclosed herein.
Figure 2B:
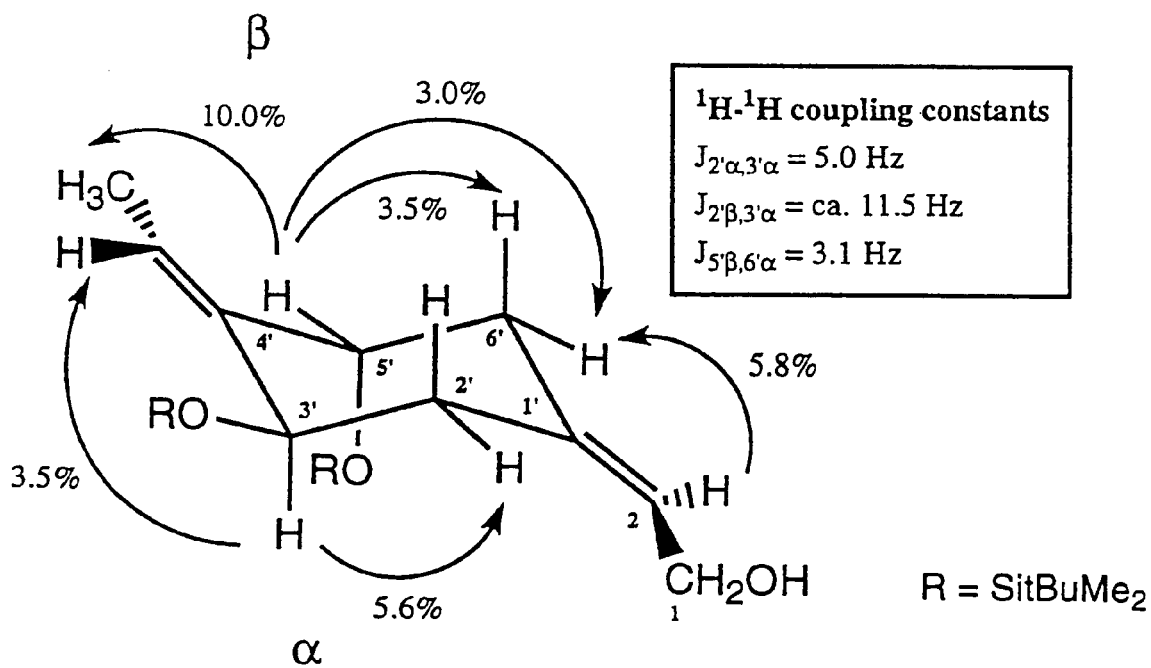

The strategy of the synthesis of 2-substituted 19-norvitamins was based on Lythgoe-type Wittig-Horner coupling. Since the corresponding C,D-ring ketones were available, attention was focused on the synthesis of the phosphine oxide A-ring synthons (Scheme 1 and 2). Configurations of the ethylidene unit at C'-4 in the isomeric compounds 16, 17 (FIG. 2) and 17, 18, as well as their preferred conformations, were determined by analysis of $^1H$ NMR spectra, NOE measurements and spin decoupling experiments.

The Wittig-Horner reaction of the conjugate base of 20 with the protected 25-hydroxy Grundmann's ketone 20 produced 19-norvitamin D compound 21 in a very high yield, i.e. 91% (Scheme 3), but-the yield of an analogous coupling of the isomeric phosphine oxide 19 was very low, i.e. 13%. The obtained condensation products 21 and 22, following deprotection, gave 2-ethylidene-19-norvitamins 4a and 5a. Considering the low yield of the Wittig reaction of the cyclohexanone 13, leading to ethylidene compounds 14 and 15 (Scheme 2), an alternative synthetic approach was sought.

Thus, the carbonyl group in 13 was protected as O-trimethylsilyl hemimethylthioketal and the corresponding phosphine oxides 25 were efficiently synthesized (Scheme 4). Coupling of their anions with the hydrindanone 26 (Scheme 5) afforded the protected 19-norvitamin D compound 27 in a high yield. This, after deprotection of 2-oxo group, Wittig reaction and subsequent hydrolysis was converted to (20S)-2-ethylidene-19-norvitamins 4b and 5b. The selective catalytic hydrogenation of 2-ethylidene analogs 4a, b and 5a, b (Scheme 6) provided the corresponding 2-ethyl-19-norvitamins 6a, b and 7a, b, which were easily separated by HPLC.

Stereochemistry at C-2 in the synthesized vitamin D compounds was tentatively assigned on the basis of conformational analysis, molecular modeling studies, and 500 MHz $^1$H NMR spectroscopy.

EXAMPLE 2

Conformational Analysis

Figure 3A:
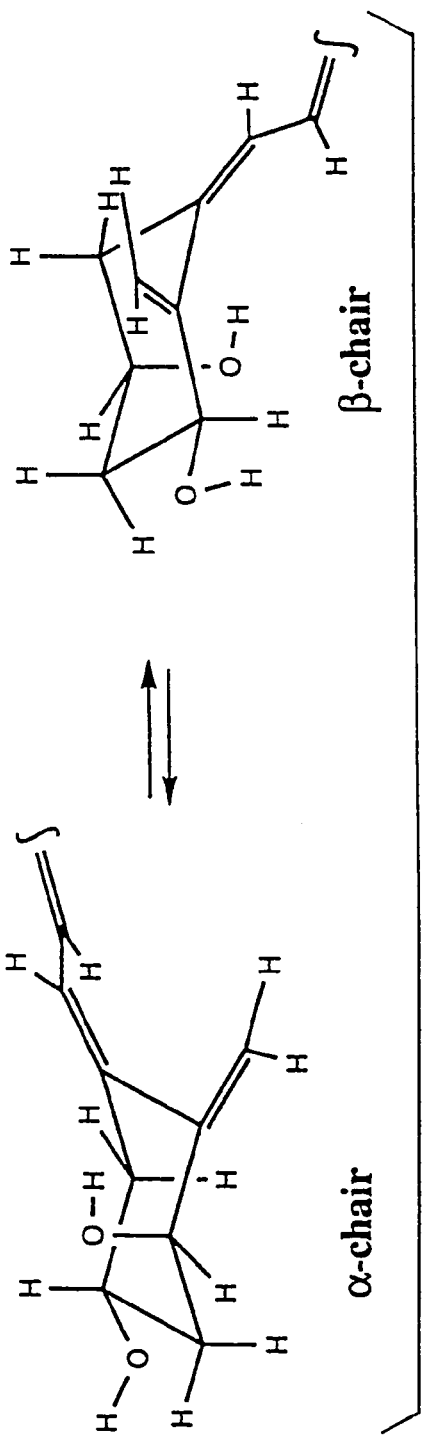
FIG. 3a illustrates the α-and β-forms of the A-ring chair conformers for vitamin D compounds in solutions.
Figure 3B:
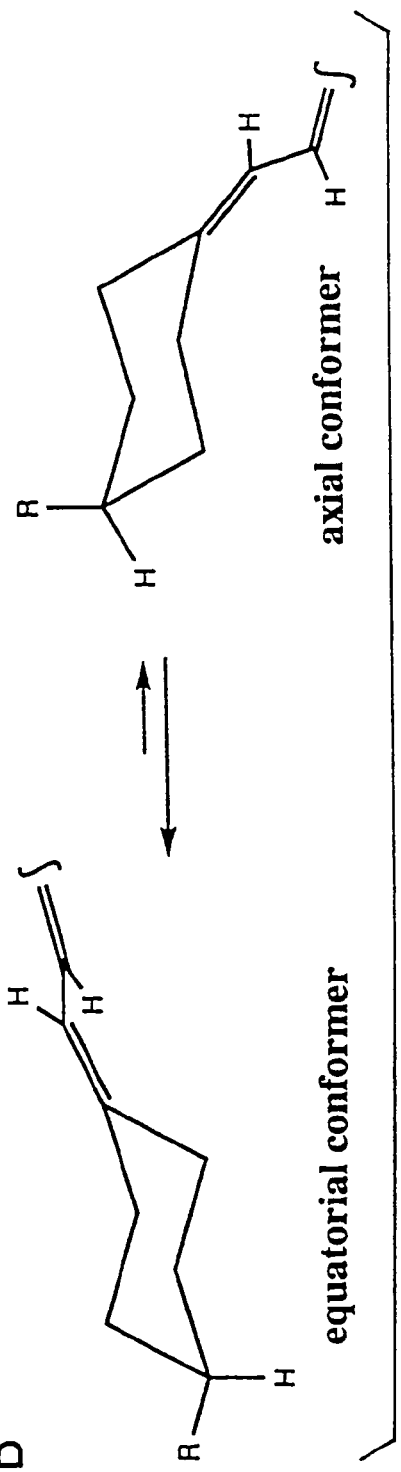
FIG. 3b illustrates that the presence of bulky 2-alkyl substituents, characterized by large conformational free energy A values, shifts the A-ring conformational equilibrium of the synthesized 2-ethyl-19-nor-vitamins toward the conformers with the equatorial C(2)-substituents.
Figure 3C:
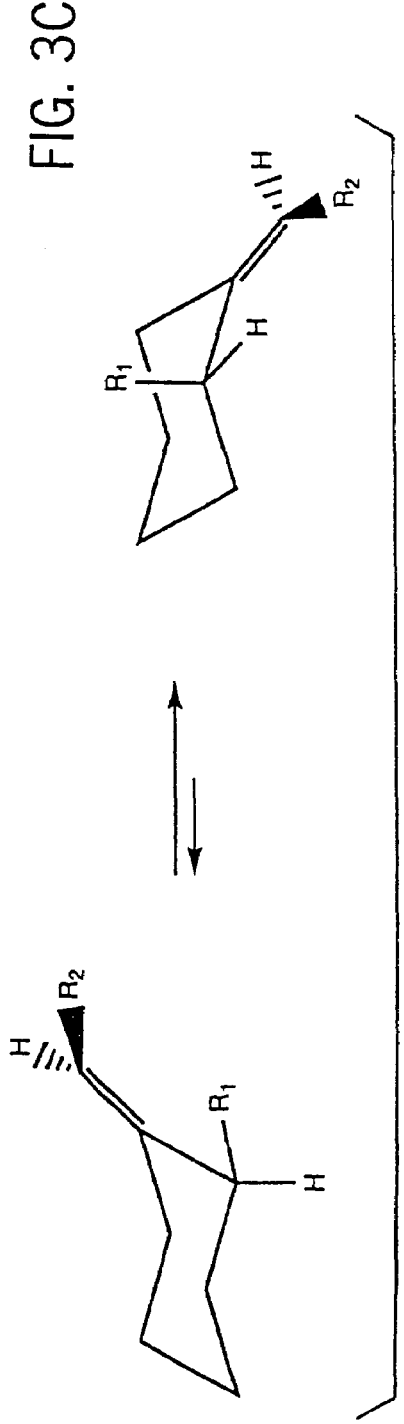
FIG. 3c illustrates that a strong interaction (designated as $A^{(1,3)}$-strain) exists between the methyl group from the ethylidene moiety and equatorial hydroxyls at C-1 or C-3, and results in a strong bias toward conformers with an axial orientation of this hydroxy group to which the methyl from ethylidene fragment is directed.
Figure 4A:
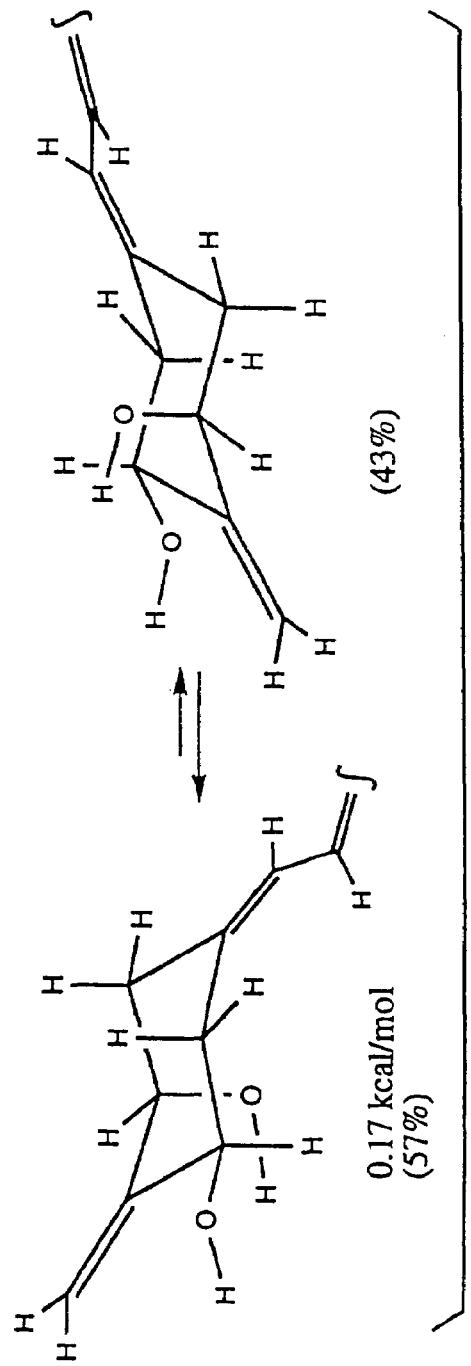
FIG. 4 illustrates the conformational equilibrium in ring A of 2-methylene-19-norvitamin 2 (a) and the preferred, energy minimized (PC MODEL 6.0, Serena Software)
Figure 4C:
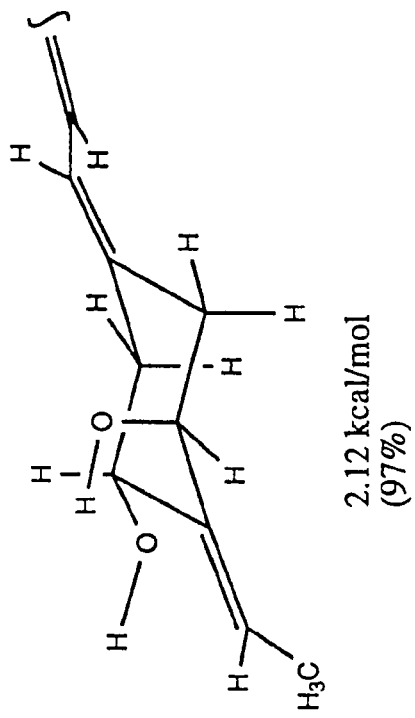
Figure 4E:
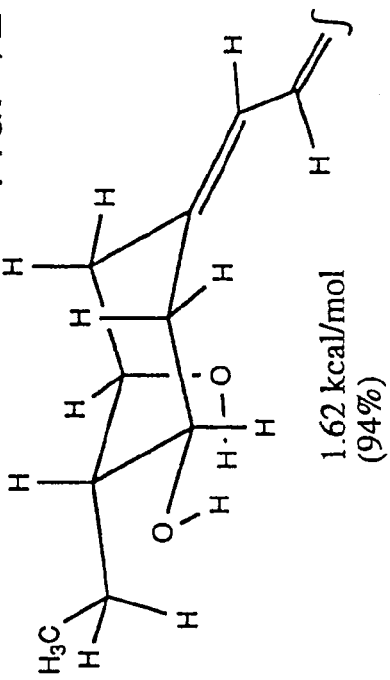
Figure 4B:
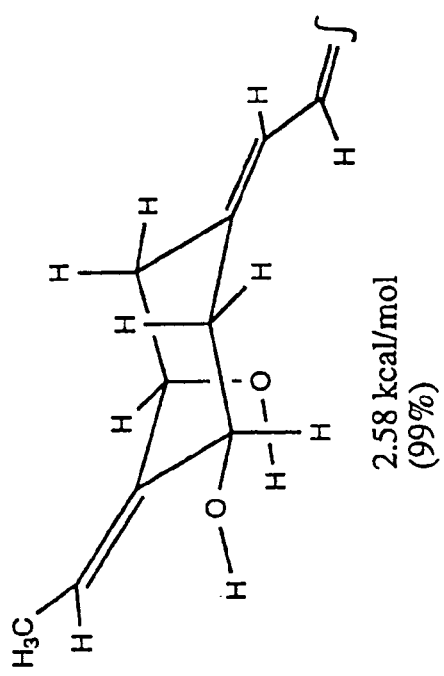
Figure 4D:
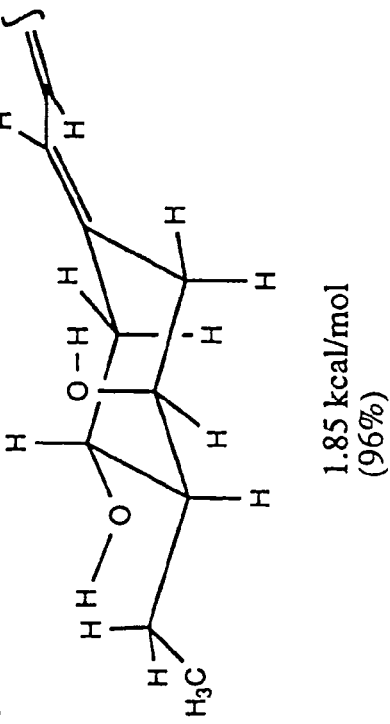

It has been established that vitamin D compounds in solutions exist as a mixture of two rapidly equilibrating A-ring chair conformers abbreviated as α-and β-forms (FIG. 3a). Presence of bulky 2-alkyl substituents, characterized by large conformational free energy A values (FIG. 3b), shifts the A-ring conformational equilibrium of the synthesized 2-ethyl-19-norvitamins toward the conformers with the equatorial C(2)-substituents. In the obtained 2-ethylidene-19-norvitamin D compounds, an additional strong interaction (designated as $A^{(1,3)}$-strain, FIG. 3c) is involved, existing between the methyl group from the ethylidene moiety and equatorial hydroxyls at C-1 or C-3. It results in the strong bias toward conformers with an axial orientation of this hydroxy group to which the methyl from ethylidene fragment is directed.

Conformational equilibrium in ring A of 2-methylene-19-norvitamin 2 (a) and-the preferred, energy minimized (PC MODEL 6.0, Serena Software) A-ring conformations of the synthesized analogs: 4a, b (b), 5a, b (c), 6a, b :(d) and 7a, b (e) are shown in FIG. 4. The steric energy differences between the preferred conformers and their partners with the inverted chair forms (calculated for model compounds lacking side chain) are given. The corresponding percentage populations (in parentheses) of conformers are given for room temperature (25° C.).

EXAMPLE 3

Biological Evaluation

The synthesized vitamins were tested for their ability to bind the porcine intestinal vitamin D receptor. The presented results (FIG. 5a) indicate that 2-ethylidene-19-norvitamins, possessing methyl group from ethylidene moiety directed toward C-3, i.e. trans in relation to C(6)—C(7) bond (isomers E), are more active than 1α,25-$(OH)_2D_3$ in binding to VDR, whereas their counterparts with cis relationship between ethylidene methyl substituent and C(7)-H group (isomers Z) exhibit significantly reduced affinity for the receptor. The competitive binding analysis showed also that 2α-ethyl-19-norvitamins bind the receptor better than their isomers with 2β-ethyl substituents (FIG. 5b). In the next assay, the cellular activity of the synthesized compounds was established by studying their ability to induce differentiation of human promyelocyte HL-60 cells into monocytes. E isomer of (20S)-2-ethylidene-19-norvitamin $D_3$ (FIG. 6a) and both 2α-ethyl-19-norvitamins (FIG. 6b) are more potent than 1α,25-$(OH)_2D_3$ in this assay, whereas the remaining tested compounds are almost equivalent to the hormone.

Both E isomers of 2-ethylidene-19-norvitamins, when tested in vivo in rats (Table 1) exhibited very high calcemic activity, the (20S)-compound being especially potent. On the contrary, isomeric Z compounds are significantly less active. 2-ethyl-19-norvitamins have some ability to mobilize calcium from bone but not to the extent of the hormone 1, while being inactive in intestine. The only exception is 2α-ethyl isomer from 20S-series that shows strong calcium mobilization response and marked intestinal activity.

TABLE 1

Support of Intestinal Calcium Transport and Bone Calcium Mobilization
By 2-Substituted Analogs of 1α,25-Dihydroxy-19-norvitamin $D_3$
In Vitamin D-Deficient Rats on a Low-Calcium Diet[a]

| compound | compd. no. | amount (pmol) | Ca transport S/M (mean ± SEM) | Serum Ca (mean ± SEM) |
|---|---|---|---|---|
| none (control) | | 0 | 3.0 ± 0.7 | 4.3 ± 0.1 |
| 1α,25-$(OH)_2D_3$ | 1 | 130 | 5.5 ± 0.5 | 5.1 ± 0.3 |
| | | 260 | 5.9 ± 0.4 | 5.8 ± 0.3 |
| 2-ethylidene-19-nor-1α,25-$(OH)_2D_3$ (E-isomer) | 4a | 65 | 5.0 ± 0.4 | 4.5 ± 0.1 |
| | | 130 | 6.8 ± 0.4 | 5.2 ± 0.2 |
| 2-ethylidene-19-nor-1α,25-$(OH)_2D_3$ (Z-isomer) | 5a | 65 | 4.4 ± 0.4 | 4.4 ± 0.2 |
| | | 130 | 5.7 ± 0.9 | 4.2 ± 0.0 |
| none (control) | | 0 | 4.4 ± 0.2 | 4.1 ± 0.2 |
| 1α,25-$(OH)_2D_3$ | 1 | 130 | 4.9 ± 0.7 | 5.2 ± 0.2 |
| | | 260 | 6.0 ± 0.9 | 6.4 ± 0.4 |
| 2-ethylidene-19-nor-(20S)-1α,25-$(OH)_2D_3$ (E-isomer) | 4b | 65 | 9.0 ± 0.3 | 8.2 ± 0.3 |
| | | 130 | 5.8 ± 0.8 | 12.1 ± 0.6 |
| 2-ethylidene-19-nor-(20S)-1α,25-$(OH)_2D_3$ (Z-isomer) | 5b | 65 | 4.3 ± 0.7 | 4.0 ± 0.3 |
| | | 130 | 3.8 ± 0.3 | 4.0 ± 0.1 |
| none (control) | | 0 | 3.8 ± 0.4 | 3.9 ± 0.1 |
| 1α,25-$(OH)_2D_3$ | 1 | 260 | 6.5 ± 0.9 | 5.8 ± 0.1 |
| 2α-ethyl-19-nor-1α,25-$(OH)_2D_3$ | 6a | 260 | 4.0 ± 0.4 | 5.1 ± 0.1 |
| 2β-ethyl-19-nor-1α,25-$(OH)_2D_3$ | 7a | 260 | 3.7 ± 0.3 | 5.0 ± 0.1 |
| 2α-ethyl-19-nor-(20S)-1α,25-$(OH)_2D_3$ | 6b | 260 | 5.0 ± 0.4 | 7.0 ± 0.1 |
| 2β-ethyl-19-nor-(20S)-1α,25-$(OH)_2D_3$ | 7b | 260 | 4.1 ± 0.3 | 5.6 ± 0.1 |

[a]Weanling male rats were maintained on a 0.47% Ca diet for one week and then switched to a low-calcium diet containing 0.02% Ca for an additional three weeks. During the last week, they were dosed daily with the appropriate vitamin D compound for seven consecutive days. All doses were administered intraperitoneally in 0.1 mL propylene glycol/ethanol (95:5). Controls received the vehicle. Determinations were made 24 hours after the last dose. There were at least six rats per group.

For treatment purposes, the novel compounds of this invention defined by formula I and/or II may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally, sublingually, intranasally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from about 0.01 μg to about 100 μg per day,.preferably from 0.1 μg to 50 μg per day of the compounds are appropriate for treatment purposes, such doses being adjusted according to the disease to be treated, its severity and the response of the subject as is well understood in the art. Since the new compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatment of psoriasis and other malignancies comprise an effective amount of one or more 2-substituted-19-nor-vitamin D compound as defined by the above formula I and/or II as the active ingredient, and a suitable carrier. An effective amount of such compounds for use in accordance with this invention is from about 0.01 μg to about 100 μg per gm of composition, and may be administered topically, transdermally, orally, sublingually, intranasally, or parenterally in dosages of from about 0.1 μg/day to about 100 μg/day.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

In its broadest application, the present invention relates to any 19-nor-analog of vitamin D which have the vitamin D nucleus. By vitamin D nucleus, it is meant a central part consisting of a substituted chain of five carbon atoms which correspond to positions 8, 14, 13, 17 and 20 of vitamin D, and at the ends of which are connected at position 20 a structural moiety representing any of the typical side chains known for vitamin D type compounds (such as R as previously defined herein), and at position 8 the 5,7-diene moiety connected to the A-ring of an active 1α-hydroxy vitamin D analog (as illustrated by formula I herein). Thus, various known modifications to the six-membered C-ring and the five-membered D-ring typically present in vitamin D, such as the lack of one or the other or both, are also embraced by the present invention.

Scheme 1

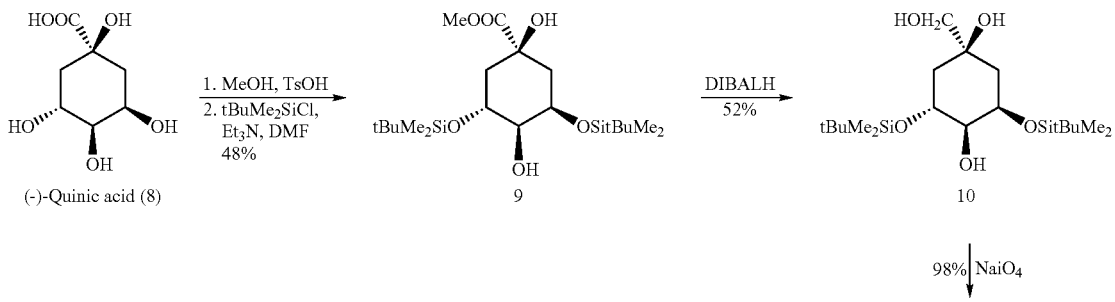

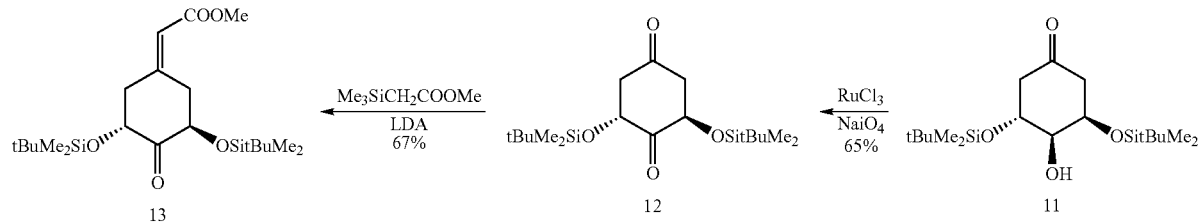
Scheme 2
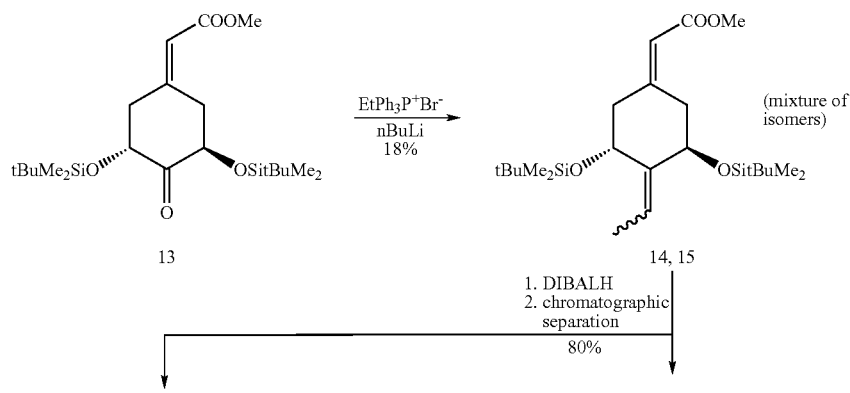
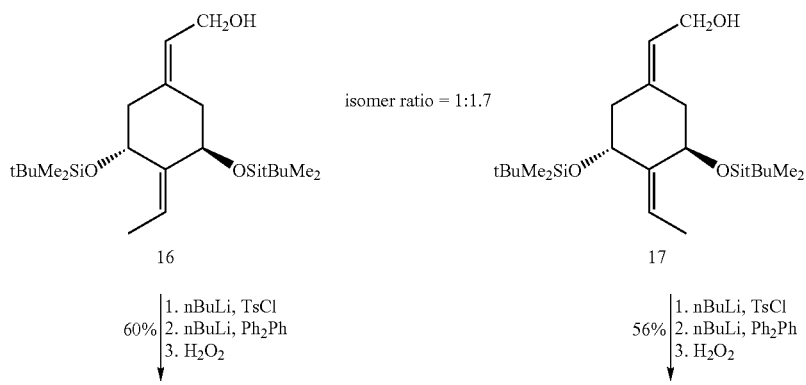
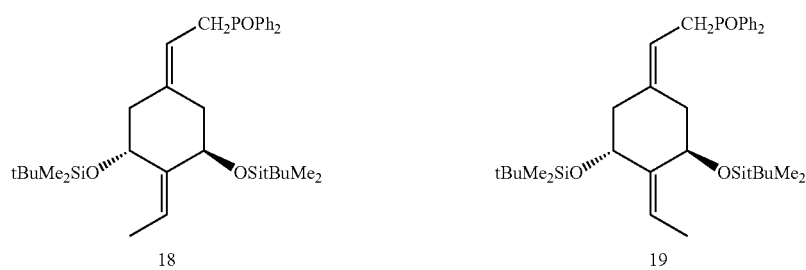

Scheme 3
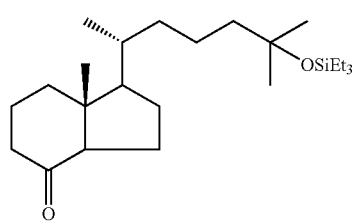
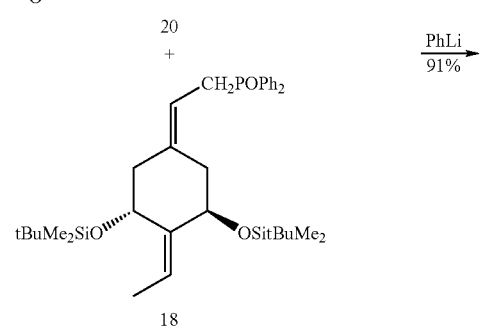
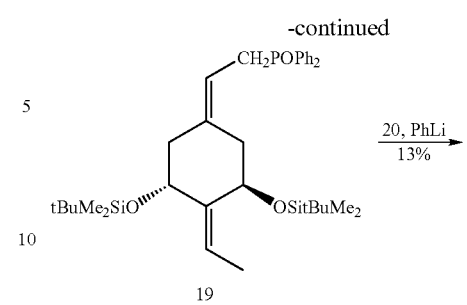
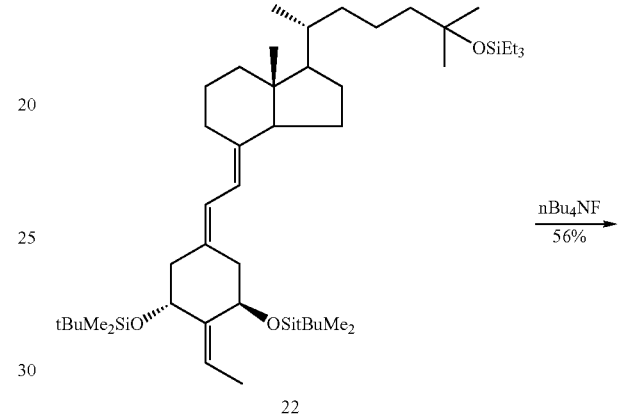
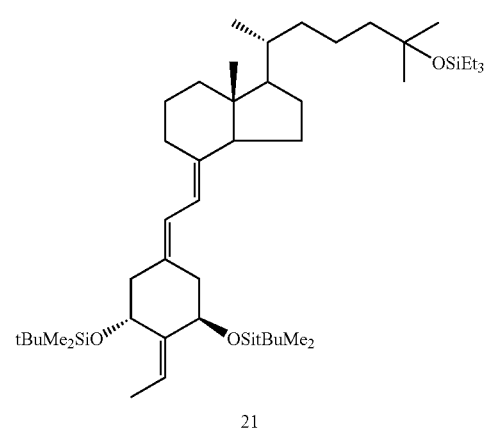
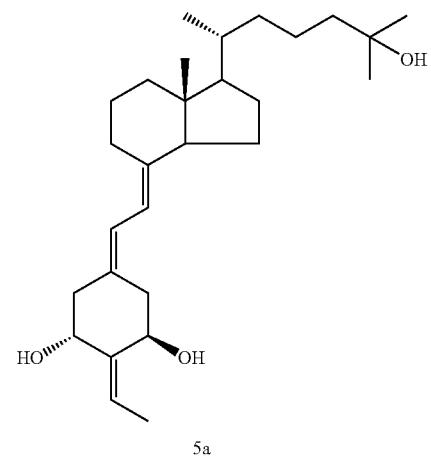
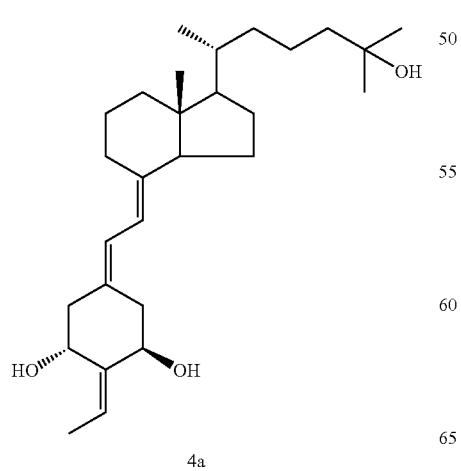
Scheme 4
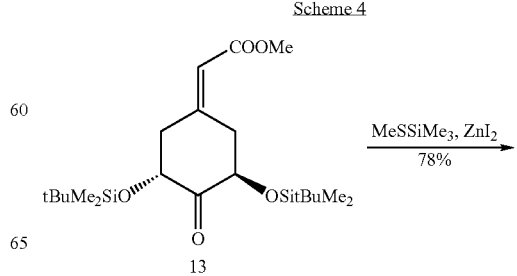

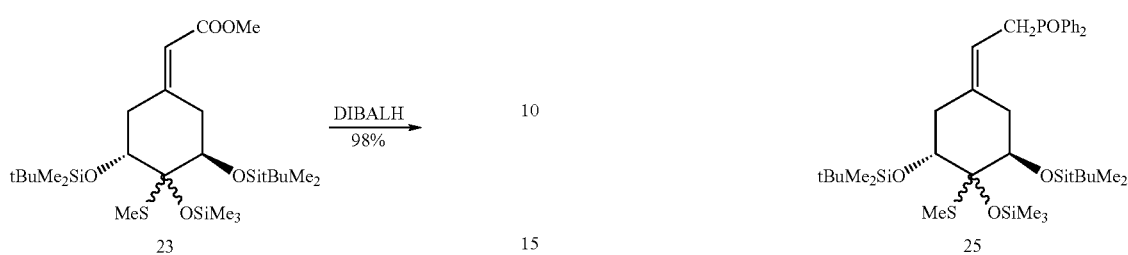
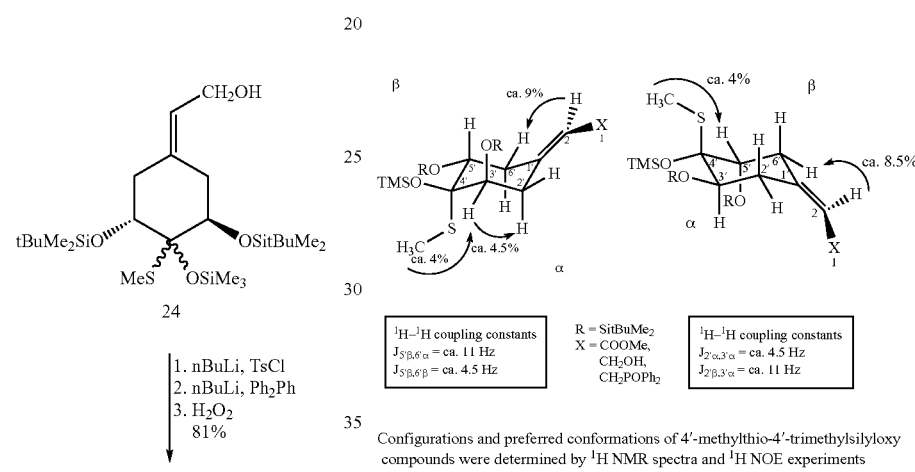
Configurations and preferred conformations of 4'-methylthio-4'-trimethylsilyloxy compounds were determined by ¹H NMR spectra and ¹H NOE experiments
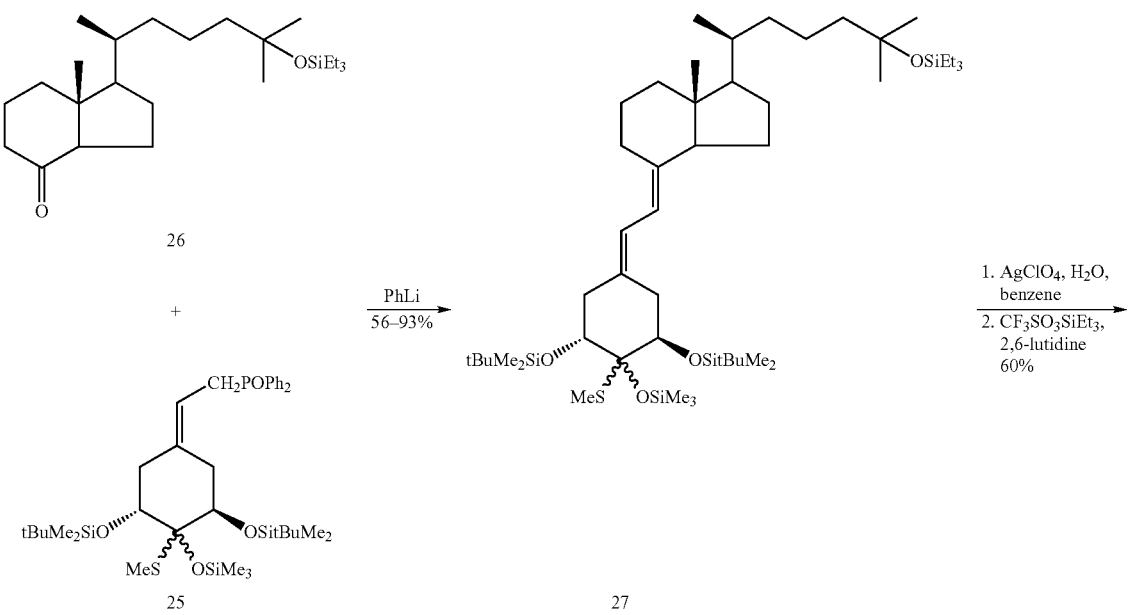
Scheme 5

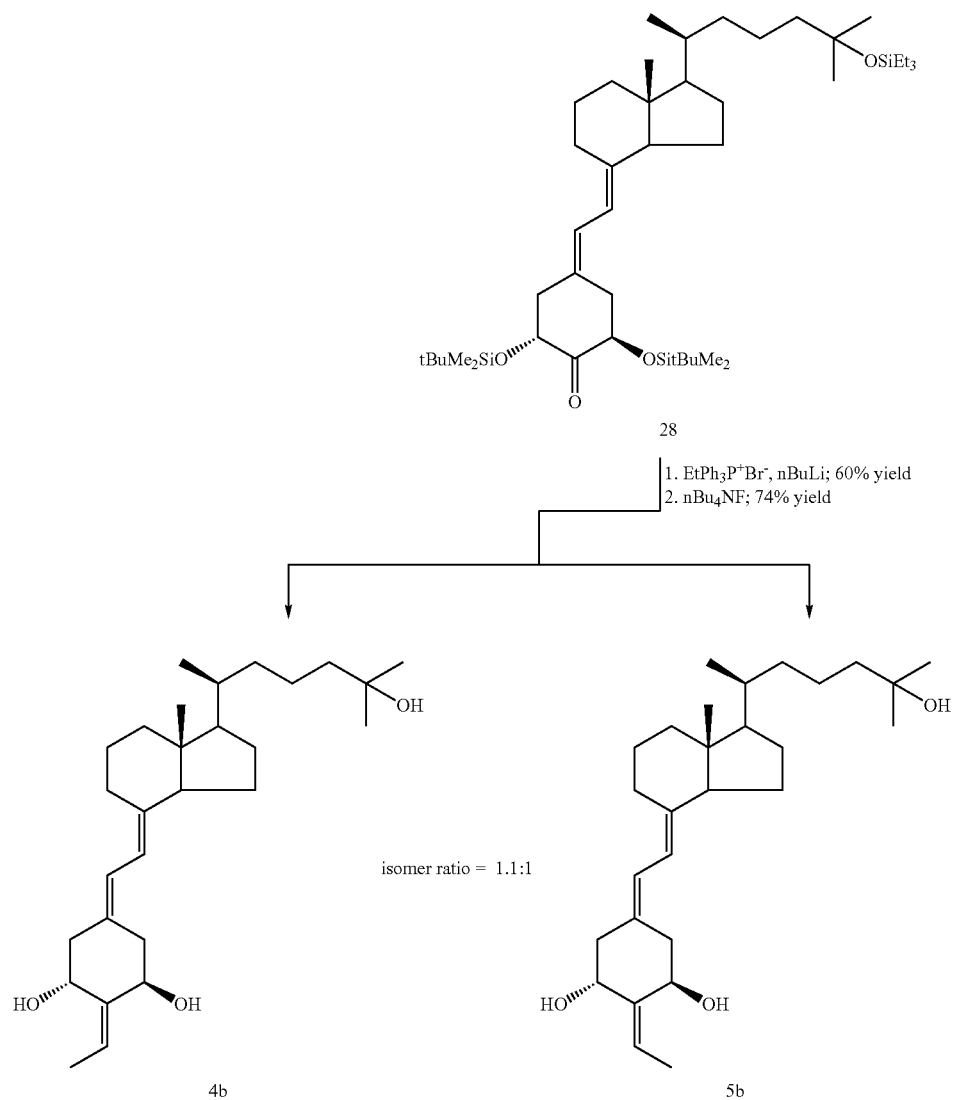
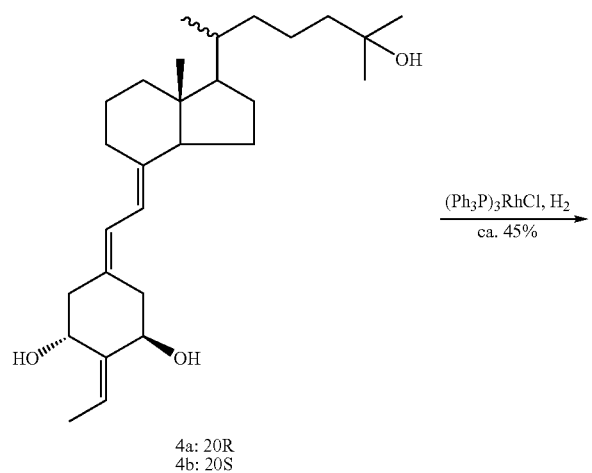
4a: 20R
4b: 20S

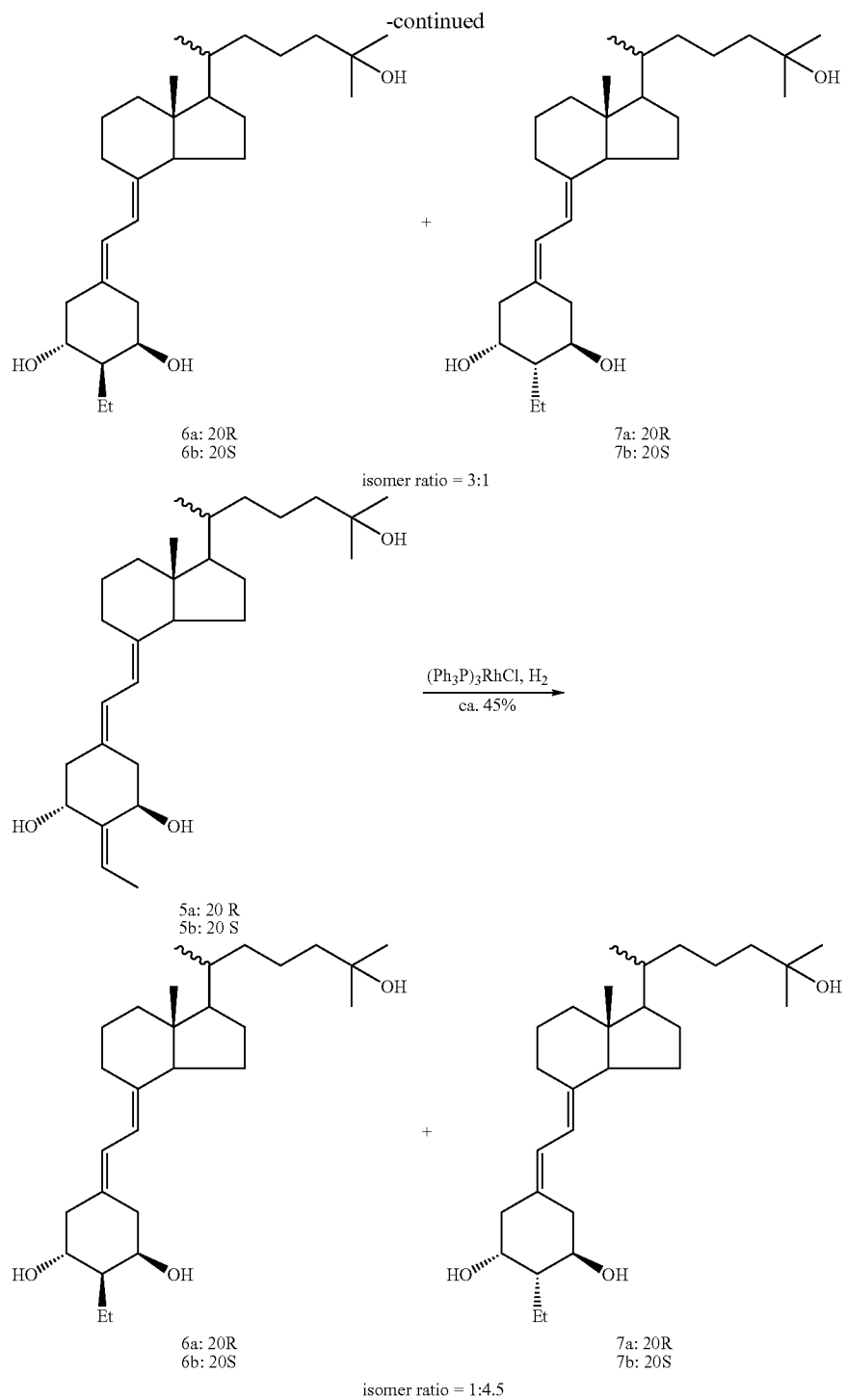

The invention claimed is:

1. A method of treating psoriasis comprising administering to a patient with psoriasis an effective amount of a compound selected from the group consisting of:
   19-nor-2α-ethyl-1α,25-dihydroxyvitamin $D_3$,
   19-nor-2β-ethyl-1α,25-dihydroxyvitamin $D_3$,
   19-nor-20(S)-2α-ethyl-1α,25-dihydroxyvitamin $D_3$,
   19-nor-20(S)-2β-ethyl-1α,25-dihydroxyvitamin $D_3$,
   19-nor-2(E)-ethylidene-1α,25-dihydroxyvitamin $D_3$,
   19-nor-2(Z)-ethylidene-1α,25-dihydroxyvitamin $D_3$,
   19-nor-2(E)-ethylidene-20(S)-1α,25-dihydroxyvitamin $D_3$, and
   19-nor-2(Z)-ethylidene-20(S)-1α,25-dihydroxyvitamin $D_3$.

2. The method of claim 1 wherein said effective amount comprises about 0.1 μg/day to about 100 μg/day of said compound.

3. The method of claim 1 wherein the compound is 19-nor-2α-ethyl-1α,25-dihydroxyvitamin $D_3$.

4. The method of claim 1 wherein the compound is 19-nor-2β-ethyl-1α,25-dihydroxyvitamin $D_3$.

5. The method of claim 1 wherein the compound is 19-nor-20(S)-2α-ethyl-1α,25-dihydroxyvitamin $D_3$.

6. The method of claim 1 wherein the compound is 19-nor-20(S)-2β-ethyl-1 α,25-dihydroxyvitamin $D_3$.

7. The method of claim 1 wherein the compound is 19-nor-2(E)-ethylidene-1α,25-dihydroxyvitamin $D_3$.

8. The method of claim 1 wherein the compound is 19-nor-2(Z)-ethylidene-1α,25-dihydroxyvitamin $D_3$.

9. The method of claim 1 wherein the compound is 19-nor-2(E)-ethylidene-20(S)-1α,25-dihydroxyvitamin $D_3$.

10. The method of claim 1 wherein the compound is 19-nor-2(Z)-ethylidene-20(S)-1α,25-dihydroxyvitamin $D_3$.

11. The method of claim 1 wherein the compound is administered orally.

12. The method of claim 1 wherein the compound is administered parenterally.

13. The method of claim 1 wherein the compound is administered transdermally.

14. The method of claim 1 wherein the compound is administered topically.

15. The method of claim 1 wherein the compound is administered in a dosage of from about 0.01 μg to about 100 μg per day.

16. The method of claim 1 wherein the compound is administered in a dosage of from about 0.1 μg to about 50 μg per day.

* * * * *